//

US007691821B2

(12) United States Patent
Desponts et al.

(10) Patent No.: US 7,691,821 B2
(45) Date of Patent: *Apr. 6, 2010

(54) INHIBITION OF SHIP TO ENHANCE STEM CELL HARVEST AND TRANSPLANTATION

(75) Inventors: Caroline Desponts, Tampa, FL (US); Joseph Wahle, Tampa, FL (US); John Ninos, Tampa, FL (US); William G. Kerr, Tampa, FL (US)

(73) Assignee: University of South Florida, Tampa, FL (US)

( * ) Notice: Subject to any disclaimer, the term of this patent is extended or adjusted under 35 U.S.C. 154(b) by 538 days.

This patent is subject to a terminal disclaimer.

(21) Appl. No.: 10/709,801

(22) Filed: May 28, 2004

(65) Prior Publication Data

US 2006/0223749 A1    Oct. 5, 2006

Related U.S. Application Data

(63) Continuation-in-part of application No. 09/955,174, filed on Sep. 19, 2001.

(60) Provisional application No. 60/320,233, filed on May 28, 2003.

(51) Int. Cl.
    *A01N 43/04*   (2006.01)
    *C12N 5/08*    (2006.01)
    *C12P 19/34*   (2006.01)
    *C07H 21/02*   (2006.01)
    *C07H 21/04*   (2006.01)

(52) U.S. Cl. .................. 514/44; 435/6; 435/91.1; 435/372; 435/455; 536/23.1; 536/24.5

(58) Field of Classification Search .................. 514/44; 435/6, 91.1, 91.31, 455, 458, 375, 372; 536/23.1, 536/24.5
    See application file for complete search history.

(56) References Cited

U.S. PATENT DOCUMENTS

| 4,603,112 | A |   | 7/1986  | Paoletti et al. |
| 4,769,330 | A |   | 9/1988  | Paoletti et al. |
| 4,777,127 | A |   | 10/1988 | Suni et al. |
| 5,017,487 | A |   | 5/1991  | Stunnenberg et al. |
| 5,166,057 | A |   | 11/1992 | Palese et al. |
| 5,804,412 | A |   | 9/1998  | Gill et al. |
| 6,025,198 | A |   | 2/2000  | Bennett et al. |
| 6,090,621 | A |   | 7/2000  | Kavanaugh et al. |
| 6,117,850 | A | * | 9/2000  | Patchen et al. ............. 514/54 |
| 6,506,559 | B1| * | 1/2003  | Fire et al. ............... 435/6 |
| 6,703,215 | B2|   | 3/2004  | Erneux et al. |
| 2002/0137711 | A1 |   | 9/2002  | Kerr |
| 2002/0165192 | A1 |   | 11/2002 | Kerr et al. |
| 2003/0114401 | A1 |   | 6/2003  | Bennett et al. |
| 2003/0143732 | A1 |   | 7/2003  | Fosnaugh et al. |
| 2003/0166282 | A1 |   | 9/2003  | Brown et al. |
| 2004/0072298 | A1 |   | 4/2004  | Sauvageau et al. |
| 2004/0235765 | A1 |   | 11/2004 | Kerr et al. |
| 2004/0259247 | A1 |   | 12/2004 | Tuschl et al. |
| 2005/0054103 | A1 |   | 3/2005  | Peled et al. |
| 2007/0224124 | A1 |   | 9/2007  | Kerr et al. |

FOREIGN PATENT DOCUMENTS

| EP | 0 345 242 A2 | 12/1989 |
| EP | 0 440 219 A1 | 8/1991 |
| GB | 2 200 651    | 8/1988 |
| WO | WO 89/01973 A2 | 3/1989 |
| WO | WO 91/02805 A2 | 3/1991 |
| WO | WO 92/06693 A1 | 4/1992 |
| WO | WO 97/10252 A1 | 3/1997 |
| WO | WO 97/12039 A2 | 4/1997 |
| WO | WO 99/32619 A1 | 7/1999 |
| WO | WO 02/24233 A2 | 3/2002 |
| WO | WO 02/44321   | 6/2002 |
| WO | WO 2009/042910 A2 | 4/2009 |

OTHER PUBLICATIONS

Opalinska, J.B. et al., Nature Rev., vol. 1, pp. 503-514 (2002).*
Chirila, R.B. et al., Biomaterials, vol. 23, pp. 321-342 (2002).*
Peracchi, A., Rev. Med. Virol., vol. 14, pp. 47-64 (2004).*
Agrawal, S. et al., Molecular Med. Today, vol. 6, pp. 72-81 (2000).*
Branch, A.D., Trends in Biochem. Sci., vol. 23, pp. 45-50 (1998).*
Hemmati-Brivanlou, A. et al., Cell, vol. 88, pp. 13-17 (1997).*
Kim, J.-H. et al., Nature, Jun. 20, 2002, pp. 1-7.*
Bjorklund, L.M. et al., Proc. Natl. Acad. Sci., vol. 99, No. 4, pp. 2344-2349 (2003).*
Kawasaki, H. et al., Neuron, vol. 28, pp. 31-40 (2000).*
Odorico, J.S. et al., stem Cells, vol. 19, pp. 193-204 (2001).*

(Continued)

*Primary Examiner*—Jane Zara
(74) *Attorney, Agent, or Firm*—Saliwanchik, Lloyd & Saliwanchik

(57) ABSTRACT

The instant invention teaches the inhibition of SHIP expression, or function, for the increased efficacy of autologous stem cell transplants. In another embodiment, interference with SHIP function can be used to temporarily expand and mobilize the hematopoietic stem cell compartment to assist with leukapheresis, to promote hematopoietic recovery after myeloablation treatments, to deplete target stem cell clones (such a leukemic clones and other tumor stem cell types), and to deplete, or damage, the repopulating ability of the endogenous hematopoietic stem cell pool in order to allow transplanted hematopoietic stem cells to better home and engraft and to promote in vivo expansion and mobilization of other organ-specific stem cell populations (e.g., mesenchymal, mammary).

10 Claims, 16 Drawing Sheets

OTHER PUBLICATIONS

Zwaka, T.P. et al., Nature online publication Feb. 10, 2003: doi:10.1038/nbt788, pp. 1-3 (2003).*

Cantley, L.C. et al. "Oncogenes and signal transduction" *Cell*, 1991, 64:281-302.

Helgason, Cheryl D. et al., Homeostasis and Regeneration of the Hematopoietic Stem Cell Pool are Altered in SHIP-Deficient Mice, Blood, 2003, 6541-3547,102(10).

Moody, Jennifer L. et al., Anemia, Thrombocytopenia, Leukocytosis, Extramedullary Hematopoiesis, and Impaired Progenitor Function in Pten+/-SHIP-/- Mice:, Blood,2004,4503-4510.

Tu, Zheng et al., Embryonic and Hematopoietic Stem Cells Express a Novel SH2-Containing Inositol 5'-Phosphatase Isoform , Blood, 2001, 2028-2038, 98(7).

Agrawal, N. et al. "RNA interference: biology, mechanism, and applications" *Microbiol. Mol. Biol. Rev.*, 2003, 67:657-685.

Bonetta, L. "RNAi: Silencing never sounded better" *Nature Methods*, 2004, 1(1):79-86.

Caplen, N.J. "RNAi as a gene therapy approach" *Expert Opin. Biol. Ther.*, 2003, 3:575-586.

Caplen, N.J. et al. "Specific Inhibition of gene expression by small double-stranded RNAs in invertebrate and vertebrate systems" *PNAS*, 2001, 98(17):9742-9747.

Damen, J.E. et al. "The 145-kDa protein induced to associate with Shc by multiple cytokines is an inositol tetraphosphate and phosphatidylinositol 3,4,5-trisphosphate 5-phosphatase" *Proc. Natl. Acad. Sci USA*, 1996, 93:1689-1693.

Elbashir, S. at al. "Duplexes of 21-nucleotide RNAs mediate RNA interference in cultured mammalian cells" *Nature*, 2001, 411:494-498.

Elbashir, S. et al. "RNA interference is mediated by 21- and 22-nucleotide RNAs" *Genes & Development*, 2001, 15:188-200.

Fire, A. et al. "Potent and specific genetic interference by double-stranded RNA in *Caenorhabditis elegans*" *Nature*, 1998, 391:806-811.

Harborth, J. et al. "Identification of essential genes in cultured mammalian cells using small interfering RNAs" *J. Cell Sci.*, Dec. 2001, 114(Pt. 24):4557-4565.

Liu, Q. et al. "Molecular cloning and chromosomal localization in human and mouse of the SH2-containing inositol phosphatase, INPP5D (SHIP)" *Genomics*, 1997,39:109-112.

Montgomery, M.K. et al. "RNA as a target of double-stranded RNA-mediated genetic interference in *Caenorhabditis elegans*" *Proc. Natl. Acad. Sci. USA*, 1998, 95:15502-15507.

Svoboda, P. et al. "Selective reduction of dormant maternal mRNAs in mouse oocytes by RNA interference" *Development*, 2000, 127:4147-4156.

Tuschl, T. et al. "RNA interference and small interfering RNAs" *Chembiochem*, 2001, 2(4):239-245.

Tuschl, T. et al. "Targeted mRNA degradation by double-stranded RNA in vitro" *Genes & Development*, 1999, 13:3191-3197.

Ware, M.D. et al. "Cloning and characterization of human SHIP, the 145-kD inositol 5-phosphatase that associates with SHC after cytokine stimulation" *Blood*, 1996, 88:2833-2840.

Zamore, P. et al. "RNAi: double-stranded RNA directs the ATP-dependent cleavage of mRNA at 21 to 23 nucleotide intervals" *Cell*, 2000, 101:25-33.

Hannon, G.J. and Rossi, J.J. "Unlocking the potential of the human genome with RNA interference" *Nature*, 2004, 431:371-378.

Hemann, M.T. et al. "An epi-allelic series of p53 hypomorphs created by stable RNAi produces distinct tumor phenotypes in vivo" *Nature Genetics*, 2003, 33:396-400.

Opalinska, J.B. and Gewirtz, A.M. "Nucleic-acid therapeutics: Basic principles and recent applications" *Nature Reviews*, 2002, 1:503-514.

Pera, M.F. et al. "Human embryonic stem cells" *J. Cell Sci.*, 2000, 113:5-10.

Puente, X.S. et al. "Human and mouse proteases: A comparative genomic approach" *Nature Reviews*, 2003, 4:544-558.

Rauh, M.J. et al. "The role of SHIP1 in macrophage programming and activation" *Biochem. Soc. Trans.*, 2004, 32:785-788.

Rehli, M. et al. "The membrane-bound ectopeptidase CPM as a marker of macrophage maturation in vitro and in vivo" *Adv. Exp. Med. Biol.*, 2000, 477:205-216.

Rohrschneider, L.R. et al. "Structure, function, and biology of SHIP proteins" *Genes & Develop.*, 2000, 14:505-520.

Verfaillie, C.M. "Hematopoietic stem cells for transplantation" *Nature Immunology*, 2002, 3:314-317.

Zandstra, P.W. et al. "Leukemia inhibitory factor (LIF) concentration modulates embryonic stem cell self-renewal and differentiation independently of proliferation" *Biotechnol. Bioeng.*, 2000, 69:607-617.

Examination Report dated Nov. 11, 2006, issued in related European application No. 01973144.7.

Ghansah, T. at al. "Expansion of myeloid suppressor cells in SHIP-deficient mice represses allogeneic T cell responses" *J. Immunology*, 2004, 173:7324-7330.

U.S. Appl. No. 10/608,452, filed Sep. 30, 2003, Kerr et al.

U.S. Appl. No. 10/904,667, filed Nov. 22, 2004, Kerr et al.

Agrawal, S. "Antisense oligonucleotides: towards clinical trials" *TIBTECH*, 1996, 14:376-387.

Agrawal, S. and Kandimalla, E. "Antisense therapeutics: is it as simple as complementary base recognition?" *Molecular Med. Today*, 2000, 6:72-81.

Akagi, K. et al. "Cre-mediated somatic site-specific recombination in mice" *Nucleic Acids Res*, 1997, 25(9):1766-1773.

Bender, M.A. et al "Description and targeted deletion of 5' hypersensitive site 5 and 6 of the mouse β-globin locus control region" *Blood*, 1998, 92:4394-4403.

Braasch, D.A. And Corey, D.R. "Novel antisense and peptide nucleic acid strategies for controlling gene expression" *Biochemistry*, 2002, 41(14):4503-4510.

Branch, A. "A good antisense molecule is hard to find" *Trends in Biochem.*, 1998, 23:45-50.

Chirila, T. et al. "The use of synthetic polymers for delivery of therapeutic antisense oligodeoxynucleotides" *Biomaterials*, 2002, 23:321-342.

Crooke, S.T. "Basic principles of antisense therapeutics" in Antisense Res. and Application, chapter 1, pp. 1-50, S. Crooke, Ed., Springer-Verlag, 1999.

Desponts, C. et al. "MHC class I inhibitory receptors on natural killer cells recruit SHIP in an attempt to control cell survival" *FASEB Journal*, Mar. 20, 2002, 16(4):A706, abstract.

Evans, D.J. et al. "An engineered poliovirus chimaera elicits broadly reactive HIV-1 neutralizing antibodies" *Nature*, 1989, 339:385-388.

Fisher-Hoch, S.P. et al. "Protection of rhesus monkeys from fatal Lassa fever by vaccination with recombinant vaccinia virus containing the Lassa virus glycoprotein gene" *PNAS*, 1989, 86:317-321.

Gewirtz, A.M. et al. "Facilitating oligonucleotide delivery: Helping antisense deliver on its promise" *Proc. Natl. Acad. Sci. USA*, 1996, 93:3161-3163.

Ghansah, T. et al "A role for the SH2-containing Inositol phosphatase in the biology of natural killer cells and stem cells" Activating and Inhibitory Immunoglobulin-like Receptors, 2001, pp. 129-140.

Ghansah, T. et al. "Target disruption of Src homology 2-containing 5' inositol phosphatase (SHIP) alters PI3K/AKT and MAPK signal transduction pathways in murine natural killer cells" *FASEB Journal*, Mar. 20, 2002, 16(4):A706, abstract.

Ghansah, T. et al. "The Src homology 2 containing inositol phosphatase is vital for the function and homeostatis of Natural Killer cells" *FASEB Journal*, Mar. 7, 2001, 15(4):A655, abstract.

Guzman, R.J. et al. "Molecular and cellular cardiology/receptors: efficient and selective adenovirus-mediated gene transfer into vascular neointima" *Circulation*, 1993, 88(6):2838-2848.

Hawkins, P.T. et al. "Platelet-derived growth factor stimulates synthesis of PtdIns(3,4,5)P$_3$ by activating a PtdIns(4,5)P$_2$ 3-OH kinase" *Nature*, 1992, 358:157-910.

Held, W. et al. "Transgenic expression of the Ly49A natural killer cell receptor confers class I major histocompatibility complex (MHC)-specific inhibition and prevents bone marrow allograft rejection" *J. Exp. Med.*, 1996, 184(5):2037-2041.

Helgason, C.D. et al. "Targeted disruption of SHIP leads to hemopoietic perturbations, lung pathology, and a shortened life span" *Genes & Dev.*, 1998, 12(11):1610-1620.

Huber, M. et al. "The src homology 2-containing inositol phosphatase (SHIP) Is the gatekeeper of mast cell degranulation" *Proc. Natl. Acad. Sci. USA*, 1998, 95(19):11330-11335.

Jefferson, A.B. et al. "Properties of type II inositol polyphosphate 5-phosphatase" *J. Biol. Chem.*, 1995, 270(16):9370-9377.

Jen, K-Y and Gewirtz, A.M. "Suppression of gene expression by targeted disruption of messenger RNA: Available options and current strategies" *Stem Cells*, 2000, 18:307-319.

Jolly, D. et al. "Viral vector systems for gene therapy" *Cancer Gene Therapy*, 1998, 1(1):51-64.

Kass-Eisler, A. et al. "Quantitative determination of adenovirus-mediated gene delivery to rat cardiac myocytes in vitro and in vivo" *PNAS*, 1993, 90:11498-11502.

Kerr, William G. et al., Critical Role for SHIP in engraftment of histo-incompatible stem cells, Oncology Research, 2001, 12:285.

Klippel, A. et al. "Membrane localization of phosphatidylinositol 3-kinase is sufficient to activate multiple signal-transducing kinase pathways" *Mol. Cell. Biol.*, 1996, 16(8):4117-4127.

Koh, C. et al. "Augmentation of antitumor effects by NK cell inhibitory receptor blockade in vitro and in vivo" *Blood*, 2001, 97(10):3132-3137.

Kolls, J. et al. "Prolonged and effective blockade of tumor necrosis factor activity through adenovirus-mediated gene transfer" *PNAS*, 1994, 91:215-219.

Lanier, L.L. "NK cell receptors" *Annual Rev of Immunology*, 1998, 16:359-393.

Liu, L. et al. "The Src homology 2 (SH2) domain of SH2-containing inositol phosphatase (SHIP) is essential for tyrosine phosphorylation of SHIP, its association with Shc, and its induction of apoptosis" *J. Biol. Chem.*, 1997, 272:8983-8988.

Liu, Q. et al. "SHIP is a negative regulator of growth factor receptor-mediated PKB/Akt activation any myeloid cell-survival" *Genes & Dev.*, 1999, 13(7):786-791.

Liu, Q. et el. "The inositol polyphosphate 5-phosphatase SHIP is a crucial negative regulator of B cell antigen receptor signaling" *J. Exp. Med.*, 1998, 188(7):1333-1342.

Lotzova, E. et al. "Prevention of Rejection of Allogeneic Bone Marrow Transplants by NK-1.1 Anti Serum" *Transplantation*, 1983, 35(5):490-494.

Lucas, D.M. and Rohrschneider, L. "A novel spliced form of SH2-containing inositol phosphatase is expressed during myeloid development" *Blood*, 1999, 93(6):1922-1933.

Okada, H. et al. "Cutting edge: Role of the inositol phosphatase SHIP in B cell receptor-induced $Ca^{2+}$ oscillatory response" *J. Immunol.*, 1998, 161:5192-5132.

Overbaugh, J. et al. "Molecular cloning of a feline leukemia virus that induces fatal immunodeficiency disease in cats" *Science*, 1988, 239:906-910.

Palu, G. et al. "In pursuit of new developments for gene therapy of human diseases" *J. Biotech*, 1999, 68:1-13.

Pihl-Carey, K. "Disease drug fails in phase III" *BioWorld Today*, 1999, 10:1-2.

Poznansky, M. et al. "Gene transfer into human lymphocytes by a defective human immunodeficiency virus type 1 vector" *J. Virol.*, 1991, 65:532-536.

Ruggeri, L. et al. "Role of natural killer cell alloreactivity in HLA-mismatched hematopoietic stem cell transplantation" *Blood*, 1999, 94(1):333-339.

Sabin, A.B. and Boulger, L.R. "History of Sabin attenuated poliovirus oral live vaccine strains" *J.. of Biol. Standardization*, 1973, 1:115-118.

Samulski, R.J. et al. "Helper-free stocks of recombinant adeno-associated viruses: normal integration does not require viral gene expression" *J. Vir.*, 1989, 63(9):3822-3828.

Stephens, L.R. et al. "Agonist-stimulated synthesis of phosphatidylinositol(3,4,5)-trisphosphate: a new intracellular signaling system?" *Biochim. Biophys Acta*, 1993, 1179:27-75.

Tamm, I. et al. "Antisense therapy in oncology: new hope for an old idea?" *The Lancet*, 2001, 358:489-497.

Wang, C.Y. and Huang, L. "pH-sensitive immunoliposomes mediate target-cell-specific delivery and controlled expression of a foreign gene in mouse" *PNAS*, 1987, 84:7851-7855.

Wang, J-W. et al. "Influence of ZSHIP on the NK Repertoire and Allogeneic Bone Marrow Transplantation" *Science*, 2002, 295(5562):2094-2097.

Wolf, I et al. "Cloning of the genomic locus of mouse SH2 containing inositol 5-phosphatase (SHIP) and a novel 110-kDa splice isoform, SHIPδ" *Genomics*, 2000, 69(1):104-112.

Yokoyama, W.M. "Natural killer cell receptors" *Current Opin in Immunology*, 1998, 10(3):298-305.

Kerr, W.G. et al. "The SH2 Containing Inositol Phosphatase (SHIP) is a Crucial Regulator of NK Cell Repertoire and Function" Abstract #34, presented at Core Research for Evolutional Science and Technology (CREST) International Symposium on Immunoglobulin-like Receptors, held Sep. 19-20, 2000, at the Sendai International Center, Sendai City, Japan.

Statement of Dr. Toshiyuki Takai, an organizer of the CREST International Symposium on Immunoglobulin-like Receptors, held Sep. 19-20, 2000.

Program and Abstracts for CREST International Symposium on Immunoglobulin-like Receptors, held Sep. 19-20, 2000.

Ahmed, N., et al. "Cytokine-Induced Expansion of Human $CD34^+$Stem/Progenitor and $CD34^+CD41^+$Early Megakaryocytic Marrow Cells Cultured on Normal Osteoblasts"*Stem Cells*, 1999, 17:92-99.

Office Action mailed Dec. 16, 2008 in U.S. Appl. No. 11/787,064, filed Apr. 13, 2007.

Office Action mailed Jan. 7, 2009 in U.S. Appl. No. 10/904,667, filed Nov. 22, 2004.

Office Action mailed Jan. 14, 2009 in U.S. Appl. No. 09/955,174, filed Sep. 19, 2001.

Geier J. et al."The Human SHIP Gene is Differentially Expressed in Cell Lineages of the Bone Marrow and Blood" *Blood*, 1997 89:1876-1885.

U.S. Appl. No. 11/451,004, filed Jun. 12, 2006, Kerr et al.

Adams, A. "RNA Therapeutics: Enter Clinical Trials" *The Scientist*, 2005, pp. 28-29, vol. 19, No. 1.

Bolland, S. et al. "SHIP Modulates Immune Receptor Responses by Regulating Membrane Association of Btk" *Immunity*, Apr. 1998, pp. 509-516, vol. 8.

De Souza, A.T. et al. "Transcriptional and phenotypic comparisons of Ppara knockout and siRNA knockdown mice" *Nucleic Acids Research*, 2006, pp. 4486-4494, vol. 34, No. 16.

Krystal, G. et al. "Molecules in focus: SHIPs ahoy" *The International Journal of Biochemistry & Cell Biology*, 1999, pp. 1007-1010, vol. 31.

Novina, C.D. et al. "The RNAi revolution" *Nature*, Jul. 2004, pp. 161-164, vol. 430.

Paroo, Z. et al. "Challenges for RNAi in vivo" *Trends in Biotechnology*, Aug. 2004, pp. 390-394, vol. 22, No. 8.

Pasquet, J.M. et al. "Phosphatidylinositol 3,4,5-trisphosphate regulates $Ca^{2+}$ entry via Btk in platelets and megakaryocytes without increasing phospholipase C activity"*EMBO Journal*, Jun. 15, 2000, pp. 2793-2802, vol. 19, No. 12.

Sawyers, C.L. "Chronic Myeloid Leukemia" *The New England Journal of Medicine*, Apr. 29, 1999, pp. 1330-1340, vol. 340, No. 17.

Office Action mailed Apr. 7, 2009 in U.S. Appl. No. 11/451,004, filed Jun. 12, 2006.

Office Action mailed Aug. 5, 2008 in U.S. Appl. No. 11/451,004, filed Jun. 12, 2006.

Office Action mailed Jun. 5, 2009 in U.S. Appl. No. 11/787,064, filed Apr. 13, 2007.

Huber, M. et al. "The role of SHIP in growth factor induced signalling" *Progress in Biophysics & Molecular Biology*, 1999, pp. 423-434, vol. 71.

Muraille, E. et al. "Distribution of the Src-homology-2-domain-containing inositol 5-phosphatase SHIP-2 in both non-haemopoietic and haemopoietic cells and possible involvement of SHIP-2 in negative signaling of B-cells" *Biochem J*, 1999, pp. 697-705, vol. 342.

Pesesse, X. et al. "The SH2 domain containing inositol 5-phosphatase SHIP2 displays phosphatidylinositol 3,4,5-trisphosphate and inositol 1,3,4,5-tetrakisphosphate 5-phosphatase activity" *FEBS Letters*, 1998, pp. 301-303, vol. 437.

Rohrschneider, L.R. et al. "Structure, function, and biology of SHIP proteins" *Genes & Development*, 2000, pp. 505-520, vol. 14.

Sly, L.M. etal. "SHIP, SHIP2, and PTEN activities are regulated in vivo by modulation of their protein levels: SHIP is up-regulated in macrophages and mast cells by lipopolysaccharide" *Experimental Hematology*, 2003, pp. 1170-1181, vol. 31.

Wisniewski, D. et al. "Neoplasia: A Novel SH2-Containing Phosphatidylinositol 3,4,5-Trisphosphate 5-Phosphatase (SHIP2) Is Constitutively Tyrosine Phosphorylated and Associated With src Homologous and Collagen Gene (SHC) in Chronic Myelogenous Leukemia Progenitor Cells" *Blood*, Apr. 1999, pp. 2707-2720, vol. 93, No. 8.

Office Action mailed Jul. 22, 2009 in U.S. Appl. No. 10/904,667 filed Nov. 22, 2004.

Office Action mailed Sep. 28, 2009 in U.S. Appl. No. 11/451,004 filed Jun. 12, 2006.

Notice of Allowance mailed Oct. 7, 2009 in U.S. Appl. No. 11/787,064 filed Apr. 13, 2007.

* cited by examiner

INHIBITION OF SHIP TO ENHANCE STEM CELL HARVEST AND TRANSPLANTATION

REFERENCE TO RELATED APPLICATIONS

This invention is based on priority document U.S. Provisional Application titled, "Inhibition of SHIP to Enhance Stem Cell Harvest and Transplantation," Application Ser. No. 60/320,233 filed on May 28, 2003. This application claims the benefit under 35 U.S.C. §120, as a continuation-in-part (CIP) of the co-pending United States application listed below, and insofar as the subject matter of each of the claims of this application is not disclosed in the manner provided by the first paragraph of 35 U.S.C. §120, I acknowledge the duty to disclose material information as defined in 37 C.F.R. §1.56 (a), which occurred between the filing date of this application and the filing date of application Ser. No. 09/955,174, Filed Sep. 19, 2001.

STATEMENT OF GOVERNMENT INTEREST

The invention described herein may be manufactured and used by the Government of the United States of America for governmental purposes without payment of any royalties thereon.

BACKGROUND ART

Technical Field

Traditional treatment for leukemia has consisted of allogeneic transplants of bone marrow (BMT) where the recipient receives tissue grafts from a healthy donor. Although allogeneic BMT has met with some success, rejection of the graft by the recipient as well as the immune response of the grafted tissue attacking the host, known as Graft-Versus-Host-Disease (GVHD), occurs in many cases. GVHD is a significant cause of mortality in allogeneic bone marrow transplant (BMT) procedures. Similarly, attempts to repress the recipient's immune system prior to the transplant leave an already weakened patient susceptible to potentially fatal post-transplant procedures.

The SH2-domain-containing Inositol 5-Phosphatase (SHIP) is a hematopoietic cell-specific protein that is activated by various cytokines and growth factors. Numerous studies using SHIP deficient mice have shown that SHIP is a negative regulator of hematopoietic cell propagation, function and survival. In essence, SHIP helps control the reproduction of immune cells in the blood known as natural killers (NK) cells. When SHIP is downregulated, or repressed, the immune system of test SHIP-deficient mice were less likely to attack and reject transplanted bone marrow from mismatched, allogeneic donors. The reverse is also true, where the immune system cells present in the transplanted tissue were less likely to attack the new host.

Down regulation of SHIP in allogeneic BMT recipients prior to transplant has shown a decrease in the number of mice suffering from GVHD. However, allogeneic methods have many variables which affect its success. In addition to deficiencies already listed, i.e. GVHD and rejection by the host, allogeneic methods are complicated by the ability to find suitable donors and the potentially lethal complications resulting from graft rejection and GVHD.

For these reasons it is preferable to treat patients with autologous transplant methods, where the patient's own stem cells, depleted of leukemic or tumor cells (including leukemic stem cells clones or tumor cells), are encouraged to grow or are removed, cultured, and re-transplanted into the original host. This method provides the benefits of eliminating the chance of host rejection or GVHD since the cells are not foreign to the body. Currently, these hematopoietic stem cell (HSC) therapies fail with significant frequency. Many times the procedure is infeasible due to the inability to acquire viable HSC from the patient for transplant. Organ-specific stem cell transplants (e.g. neural stem cells, mesenchymal stem cells) are not yet widely used clinically due to the inability to acquire these cells or due to their inability to home efficiently and engraft after transplantation.

Therefore, what is needed is an efficacious therapy that provides a long-term benefit in a wide variety of genetic, oncologic and infectious diseases in the emerging field of stem cell transplantation.

MODE FOR THE INVENTION

The instant invention teaches the inhibition of SHIP expression, or function, for the increased efficacy of autologous transplants. In addition to cancer-related therapies BM stem cells are currently thought to be an effective therapy for cardiac repair. Other tissue or organ-specific stem cells, such as neural stem cells, might also be used to treat neurological diseases that occur due to the loss of neurons in the central nervous system.

In another embodiment, interference with SHIP function can be used to temporarily expand the hematopoietic stem cell compartment to assist with leukapheresis, to promote hematopoietic recovery after myeloablation treatments, to deplete target stem cell clones (such a leukemic stem cell clones and other tumor stem cell types), and to deplete, or damage, the repopulating ability of the endogenous hematopoietic stem cell pool in order to allow transplanted hematopoietic stem cells to better home and engraft and to increase mesenchymal stem cells number in vivo and ex vivo.

The method of increasing the yield of stem cells in a patient, in vivo, for autologous transplantation, comprises the steps of administering an effective amount of SHIP inhibitor to the patient and harvesting the stem cells from the patient for autologous transplantation. In one embodiment of this method, the SHIP inhibitor is selected from the group consisting of RNA interference compounds, antisense oligonucleotides, ribozymes, DNAzymes, nucleic acid modifiers, PNAs, nonstandard nucleic acids, aptamers, decoys, oligonucleotide based gene regulation, substrate mimics, molecular inhibitors and dominant/negative mutants. The stems cells harvested for transplantation are selected from the group consisting of hematopoietic stem cells, mammary stem cells, mesenchymal and other organ specific stem cells.

In another embodiment, the present invention provides a method of increasing the yield of stem cells from a patient, ex vivo, for autologous transplantation, comprising the steps of harvesting target stem cells from the patient and contacting the target stem cells with SHIP inhibitor. The SHIP inhibitor is selected from the group consisting of RNA interference compounds, antisense oligonucleotides, ribozymes, DNAzymes, nucleic acid modifiers, PNAs, nonstandard nucleic acids, aptamers, decoys, oligonucleotide based gene regulation, substrate mimics, molecular inhibitors and dominant/negative mutants. Stems cells harvested for transplantation are selected from the group consisting of hematopoietic stem cells, mammary stem cells, mesenchymal and other organ specific stem cells.

In yet another embodiment, the present invention provides a non-invasive method for harvesting stem cells from solid organ systems such as the CNS by mobilizing these cells to the blood, comprising the steps of administering SHIP inhibitor to a patient and then harvesting the stem cells from the volume of blood by leukopherisis. The stem cells can be either hematopoietic stem cells (HSC) or non hematopoietic (e.g., CNS, mesenchymal or other organ-specific stem cells).

In yet another embodiment the present invention provides a non-invasive method of promoting recovery of a stem cell population in a patient comprising the step of administering SHIP inhibitor to the patient, possibly a patient recovering from myeloablation therapy. The administration of SHIP inhibitor is conducted over a relatively short period, such as approximately one (1) and two (2) weeks. As mentioned, the target stem cell population can be either hematopoietic or non-hematopoietic stem cells.

In another embodiment, the present invention provides a method of reducing the population of target cells comprising the step of administering an effective amount of SHIP inhibitor to a patient. The administration of SHIP inhibitor is conducted over a more prolonged period, such as approximately nine (9) and twelve (12) weeks and can be used in conjunction with chemotherapeutic agents.

BRIEF DESCRIPTION OF THE DRAWINGS

For a fuller understanding of the nature and objects of the invention, reference should be made to the following detailed description, taken in connection with the accompanying drawings, in which.

BEST MODE FOR CARRYING OUT THE INVENTION

Figure 1:
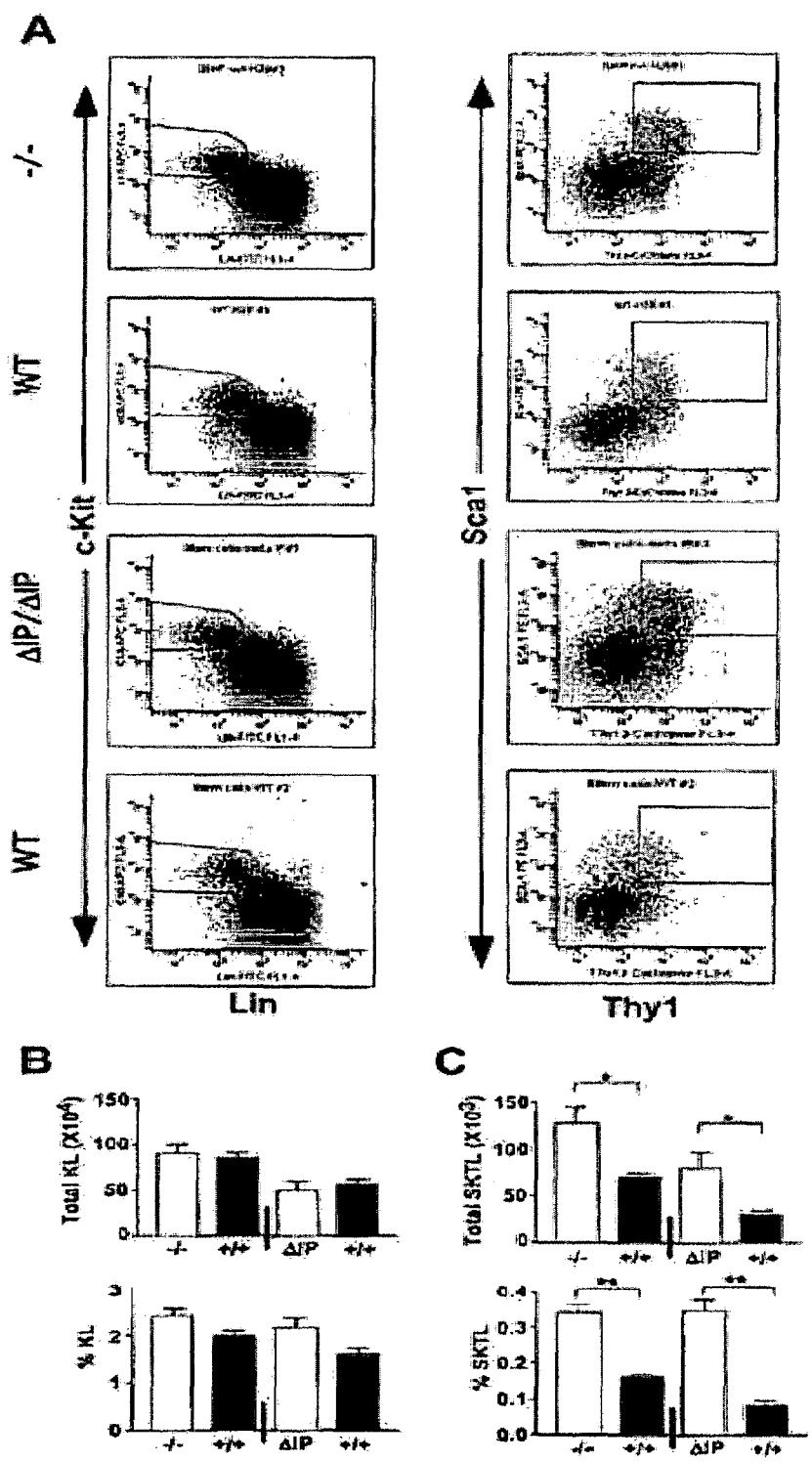
FIG. 1 illustrates how Hematopoietic stem cell (HSC) numbers are increased significantly in SHIP-deficient mice.

The present invention relates to the novel and unexpected finding that SHIP activity has a crucial role in regulating the number of hematopoietic, mammary and mesenchymal stem cells. Specifically, the present invention comprises methods for the increased efficacy of autologous stem cell transplants.

Terms: With regard to present disclosure above and below, the following terms are to be understood as follows.

SHIP—as used herein refers to the SH2-containing inositol-5-phosphatase-1. SHIP contains an amino-terminal src-homolgy domain (SH2), a 5'phosphoninositol phosphate domain, two phosphotyrosine binding consensus sequences, and a praline-rich region located in the carboxyl terminus.

Inhibition of SHIP function—as used herein refers to any genetic, or non-genetic, means for inhibiting SHIP function or expression. The term is meant to comprise any method of achieving this result known in the art. The term includes all methods known, as well as any substance which inhibits SHIP function or expression. Examples include, but are not limited to, RNA interference, antisense oligonucleotides, ribozymes, DNAzymes, nucleic acid modifiers, PNAs, nonstandard nucleic acids, aptamers, decoys, oligonucleotide based gene regulation, substrate mimics, molecular inhibitors and dominant/negative mutants.

Ex Vivo—as used herein refers to transfecting, contacting, or administering a substance to a cell outside of the body. As an example, a cell which shows expression of SHIP is removed from the host. The cell is then transfected, contacted, or administered with a substance that either inhibits SHIP expression or function. The cell is then either transplanted into the host, or allowed to propagate a new population of SHIP deficient cells, in the case of inhibition of SHIP expression, or cells in which SHIP function has been silenced (function).

Administering or Contacting—as used herein refers to the process of delivering to a cell, ex vivo, or a host, in vivo, a therapeutic substance, or a combination of several therapeutic substances. The process can include any method known in the art and is dependent on the type of substance or substances administered. Possible methods include, but are not limited to, parenteral (i.e. subcutaneously, intravenously, intramuscularly, intra-arterially, and direct injection into a tissue or organ), mucosal (i.e. intranasally), pulmonary (i.e. via inhalation), topical, via catheter (i.e. iontopheretically) or orally. Administration is usually achieved via a pharmaceutically acceptable carrier.

Gene Therapy—as used herein refers to a therapeutic method of delivery wherein the therapeutic agent is a polynucleotide capable of accomplishing a therapeutic goal when expressed as a transcript, an interfering RNA, an anti-sense polynucleotide or a polypeptide in the host or cell.

Therapeutically Effective Amount—as used herein is that amount of a substance necessary to achieve a desired therapeutic result. For example, if the therapeutic result desired is the enhanced yield of stem cells, the therapeutically effective amount is that amount that facilitates, or achieves, an increase in the total number of stem cells in a given population. The therapeutically effective amount can be a dosage administered in at least one amount and can include an administration protocol spanning several days or weeks.

Genetic Assembly—as used herein refers to any construct which is capable of modulating the expression of a target sequence or gene. Genetic assemblies can include transcriptional promoter/enhancers, locus defining elements, or any element that controls gene expression by any means (i.e. RNAi, alternate splicing, nuclear RNA export, post-translational modification of intermediaries or proteins). The genetic assembly optimally includes a sequence which is operably linked to the target sequence or gene, when expressed, and acts as a translation initiation sequence.

Autologous Transplantation

In one embodiment, the invention provides a method for increasing the yield of stem cells in a patient, in vivo, for autologous transplantation. Such a treatment is valuable for any disease, or genetic impairment, requiring treatment by bone marrow transplant (i.e. cancer, autoimmune deficiencies, HIV/AIDS), blood transplantation (e.g. mobilized stem cells), or stem cell transplant from any tissue source (stem cell transplants may come from non-BM stem cell populations, such as neural stem cells from the CNS, and therefore SHIP inhibition can increase these populations as well, as well as their mobilization to the blood (as it does for hematopoetic stem cells). The non-hematopoietic stem cells can be mobilized to the blood, which would greatly reduce the obstacles faced with collecting cells from bone marrow, brain, or other solid organs). It is known that current hematopoietic stem cell therapies face significant obstacles due to the inability to acquire sufficient numbers of hematopoietic stem cells (HSC) from the patient for transplant. Accordingly, organ-specific stem cell transplants are not currently being done routinely in a clinical setting. In addition to the difficulty in acquiring these cells, efficacious treatments are hindered by the cells inability to efficiently home and engraft after infusion into circulation.

Therefore, in one embodiment, a substance that inhibits SHIP is administered to the patient prior to harvesting of the target stem cells. After treatment has been administered for a therapeutically effective time, stem cells are collected and transplanted back into the same host. This has the advantage of avoiding both rejection by the host and Graft Versus Host Disease, wherein the immune response of the grafted tissue attacks the host. Administration of the substance can take the form of genetic assembly or a pharmaceutical agent. These may include nucleic acids, or any substance, that inhibits SHIP function or expression, or leads to the expression of any antagonist of SHIP function. The genetic assembly can be linked to a promoter and other signals directing expression of a protein SHIP antagonist. Antisense oligonucleotides are also viable assemblies. Other possible genetic assemblies include, but are not limited to, RNA interference molecules (sRNA), enzymatic inhibitors, ribozymes, DNAzymes, nucleic acid modifiers, dominant/negative mutants, PNAs (or other nonstandard nucleic acids), aptamers, SHIP specific decoys and oligo based gene regulators.

In another embodiment, the efficiency of autologous tissue transplantation is greatly enhanced by removal of the threat of rejection or GVHD in a patient, ex vivo, through inhibition of SHIP function. Here, stem cells are collected prior to inhibition of SHIP activity. After the cells are collected they are contacted with an effective amount of a substance which inhibits SHIP activity. The cells are then allowed to propagate to increase their number in the presence of the SHIP inhibitor. When a therapeutically effective population of cells is achieved the cells are transplanted back to the host.

The number of hematopoietic stem cells (HSC), mammary stem cells (MSC) and mesenchymal stem cells (MeSC) is increased in vivo in SHIP-deficient mice. Thus, inhibition of SHIP expression or activity prior to harvest, or ex vivo after harvesting, allows greater numbers of organ-specific stem cells to be used for transplant and thus ensures that an adequate dose of stem cells is available for transplantation or gene modification. In addition to this quantitative effect, SHIP deficiency increases the proportion of actively dividing stem cells and thus SHIP-deficiency also has a beneficial qualitative effect on stem cell function. SHIP-deficiency also enhances the homing ability of stem cells to the tissue sites that are necessary for their engraftment (e.g. SCF, CXCR4). SHIP is known to increase the migration of differentiated hematopoietic cells to SCF and CXCR4, therefore SHIP inhibition enhances tissue homing of stem cells after their injection or transplantation.

Particularly, the increased cycling capacity of SHIP-deficient HSC enhances their ability to repopulate a damaged organ and their ability to be transduced by various gene delivery systems. Other features of stem cells are also enhanced by SHIP deficiency, such as homing to the damaged organ or cytokine-stimulated mobilization to the blood for stem cell collection. In a similar manner, inhibition of SHIP expression or activity can also be used to increase the number of organ-specific stem cells obtained from differentiation of pluripotent stem cells (ES cells). Thus, the development of a method to specifically inhibit SHIP expression or activity is a means to enhance stem cell harvesting, gene modification, homing and collection from the peripheral blood or lymph.

EXAMPLE 1

Effects of In Vivo SHIP Deficiency on HSC

FIG. 1 shows that hematopoietic stem cell numbers are increased significantly in SHIP-deficient mice. However, the number of multipotent progenitor cells remains unaffected. FIG. 1 (A) shows FACS analysis of SKTL HSC cells and KL stem/progenitors in SHIP−/−, SHIPDIP/DIP and their WT littermates. FIG. 1(B) illustrates absolute and relative numbers of KL stem/progenitors and (C) SKTL HSC in SHIP−/−, SHIP DIP/DIP and their WT littermates. The values determined for SHIP−/− and SHIP DIP/DIP mice that are significantly different from their WT counterparts are indicated by the following symbols: *, $p<0.05$ and **, $p<0.0001$. Bone marrow cells were obtained by flushing two intact femurs and two tibias from each mouse. Cells were stained and then analyzed using a FACS Vantage (Becton Dickinson) for the presence of HSC as defined by theSca1+Thy1.2+ckit+Lin− (SKTL) HSC phenotype. There was no significant difference observed in the absolute or relative number KL stem/progenitor cells present in SHIP mutant strains and their WT counterparts. Note that the background of SHIP−/− mice is essentially C57BL6/J while the SHIP DIP/DIP are F2 (129Sv C57BL6/J). Thus, the SHIP mutation impacts HSC frequency despite differences in genetic background, further attesting to its role in regulating HSC numbers.

EXAMPLE 2

Proliferation of HSC in the Presence of SHIP Deficiency

Figure 2:
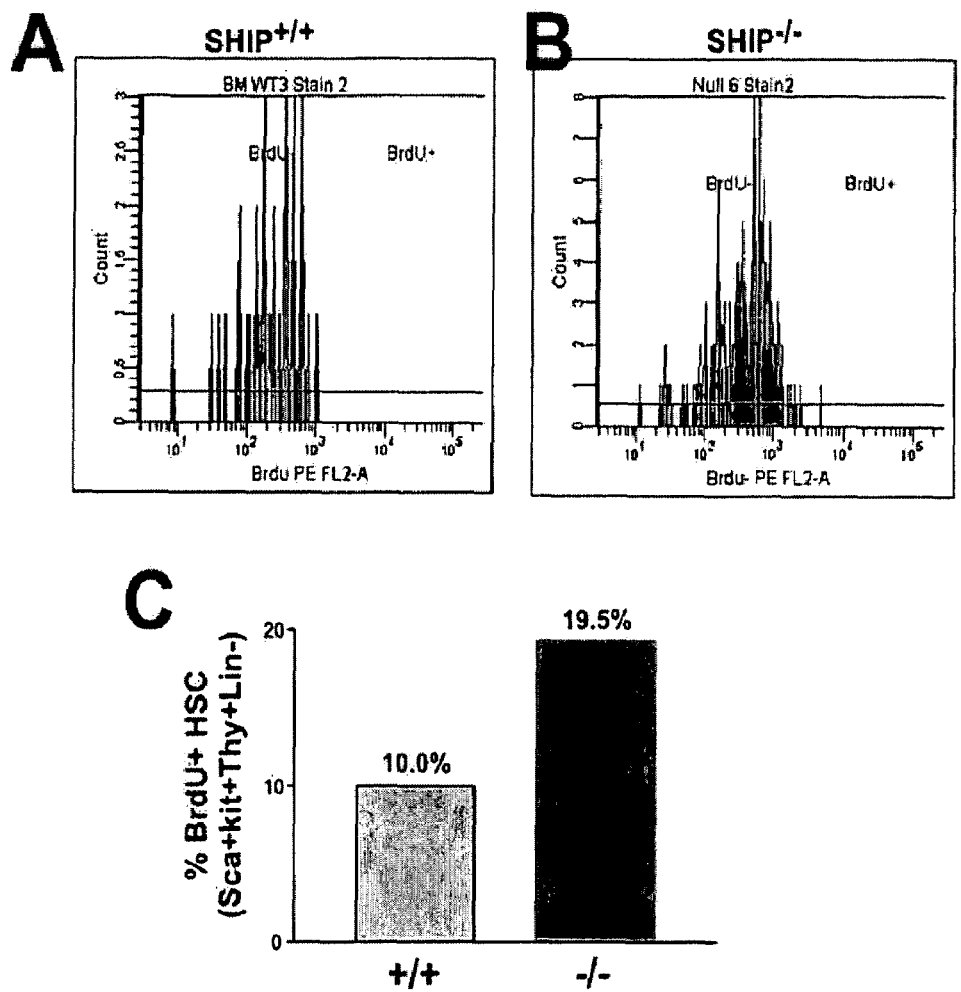
FIG. 2 illustrates how SHIP deficiency increases the number of HSC that are actively cycling.

FIG. 2 shows that a greater proportion of SHIP-deficient HSC are actively proliferating. BrdU staining in Sca+Thy1+ kit+Lin− HSC from a representative SHIP+/+ (A) and SHIP−/− (B) mouse. (C) Mean BrdU incorporation in Sca+ Thy1+kit+Lin− HSC following a 9 day BrdU pulse of SHIP−/− and SHIP+/+ mice (n=2 per genotype). The percentage of HSC positive for BrdU incorporation was determined by comparison with an isotype control Ab conjugated to PE (Pharmingen). Only HSC with BrdU staining above that seen in the isotype control were considered positive for BrdU incorporation and this fraction was used to determine the percent BrdU positive HSC. Mice were placed on drinking water containing bromodeoxyuridine (BrdU) at 1 mg/ml for 9 days. The mice were then sacrificed and bone marrow cells were isolated from intact tibia and femurs. The BM cells were initially stained with the Lin panel-FITC, c-Kit-APC, Sca1-PE-Cy7 and Thy1.2-Cychrome (eBioscience) antibodies. Following cell permeabilization, the samples were stained with anti-BrdU-PE (BD Pharmingen) and analyzed on a FACS Vantage/DIVA.

EXAMPLE 3

Effects of In Vivo SHIP Deficiency on MSC

Figure 3:
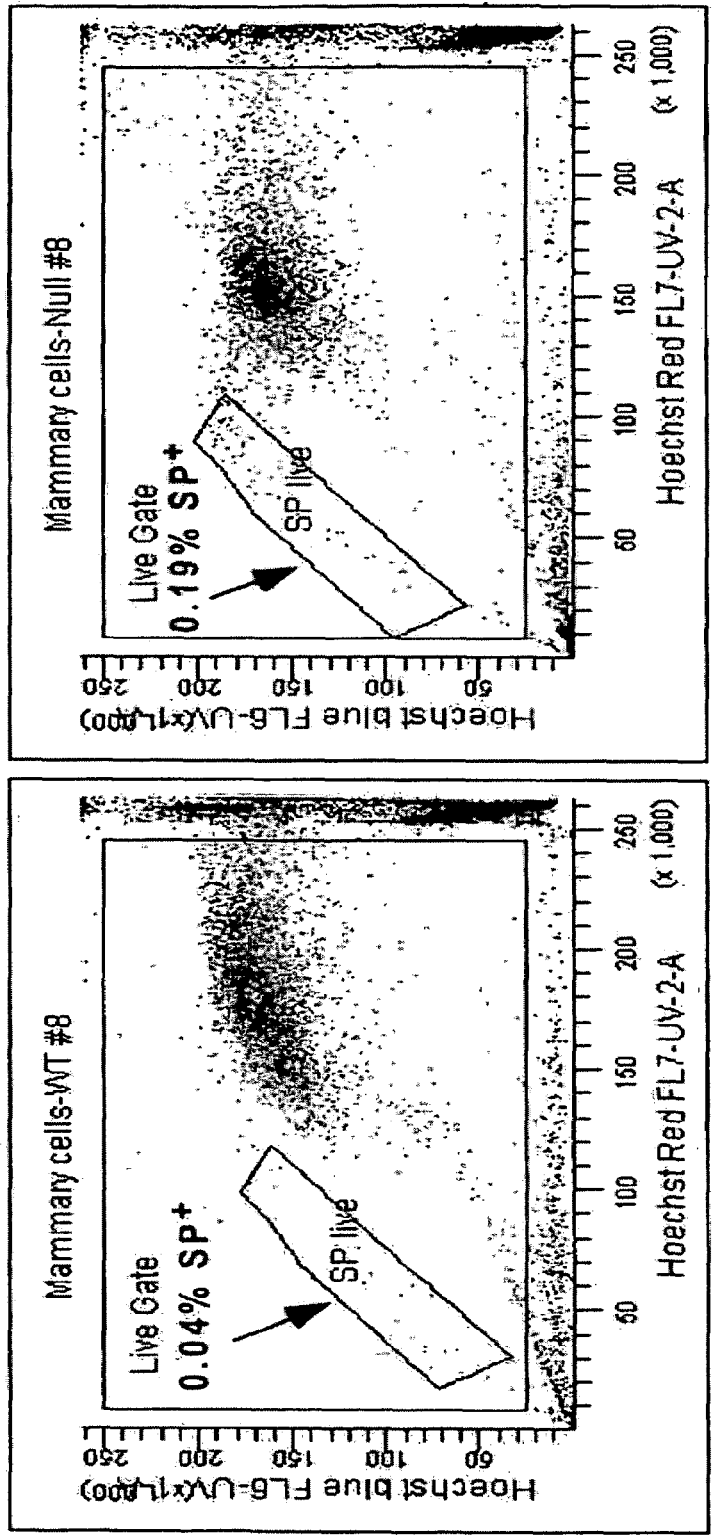
FIG. 3 illustrates how mammary stem cells (MSC) are increased significantly in SHIP-deficient mice.

FIG. 3. depicts mammary gland stem cells (MSC) as identified by the SP phenotype (Side Population) based on exclusion of Hoechst dye. Mammary glands were prepared from adult SHIP+/+ and SHIP−/− littermates and a single cell suspension was prepared. Viable cells were analyzed for exclusion of the Hoechst dye and 7AAD. The percentage of MSC present in the mammary gland of each genotype is indicated. Note that there is almost a five-fold increase in the frequency of MSC present in the SHIP−/− mammary glands.

EXAMPLE 4

Example of Predictable SHIP Inhibition In Vivo

Figure 4:
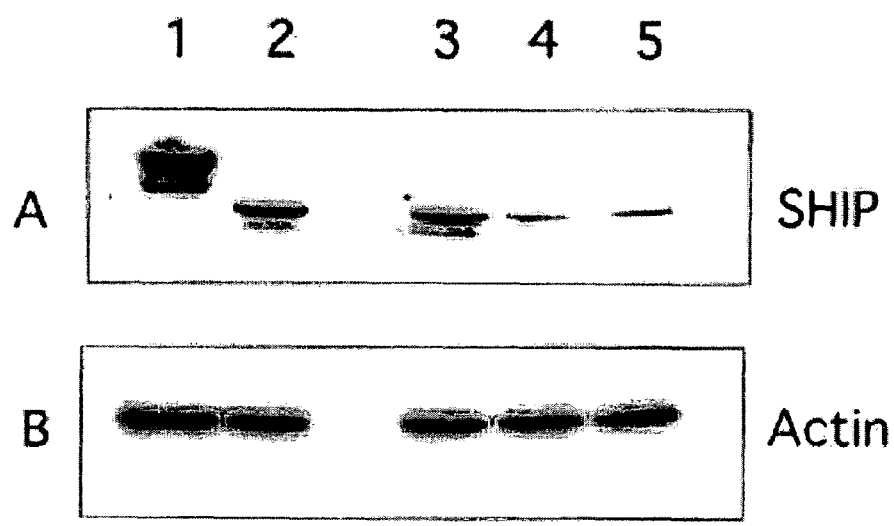
FIG. 4 illustrates a method to render primary stem cells SHIP deficient.

FIG. 4. displays one method to render primary stem cells SHIP deficient by RNA interference. Embryonic stem cells that express the SHIP gene were transfected with an irrelevant shRNA vector (Lane 3) or with two different SHIP-specific shRNA vectors (Lanes 4 and 5). The cells were then lysed and equal quantities of whole cell extracts were blotted with either anti-SHIP (Panel A) or anti-Actin (Panel B). Lane 2 shows untreated ES cells. Lane 1 shows untreated RAW264.7 cells that express the SH2 containing SHIP p135 and p145 isoforms. Panel A shows significant reduction of SHIP expression in primary ES cells after transfection of SHIP-specific shRNA vectors in the absence of selection. Please note that these vectors will also interfere with the larger SH2—containing isoforms expressed in differentiated hematopoietic cells.

Included herein are thirteen (13) SHIP1 siRNA target sequences (Seq. ID. Nos. 1-13). These sequences are predicted to have strong specificity and strong knockdown against the human SHIP1 cDNA sequence. The cDNA is about 4800+ nt (Seq. ID. No. 14). Accordingly other target sequences are available, however, those listed (13) have a strong predictability factor in vivo.

Long Term Repopulation Modulation: In addition to the present inventions unexpected findings with regard to the enhancement of stem populations in a SHIP deficient environment, the present invention also relates to the novel and unexpected finding that SHIP deficient cells experience difficulty with regard to long-term repopulation of the blood system in comparison to wild-type hematopoietic stem cells.

Therefore, in another embodiment, interference with SHIP function can be used to temporarily expand the hematopoietic stem cell compartment to assist with leukapheresis, to promote hematopoietic recovery after myeloablation treatments, to deplete target stem cell clones (such a leukemic clones and other tumor stem cell types), and to deplete, or damage, the repopulating ability of the endogenous hematopoietic stem cell pool in order to allow transplanted hematopoietic stem cells to better home and engraft and to increase mesenchymal and stem cells number in vivo and ex vivo.

Figures 5A, 5B:
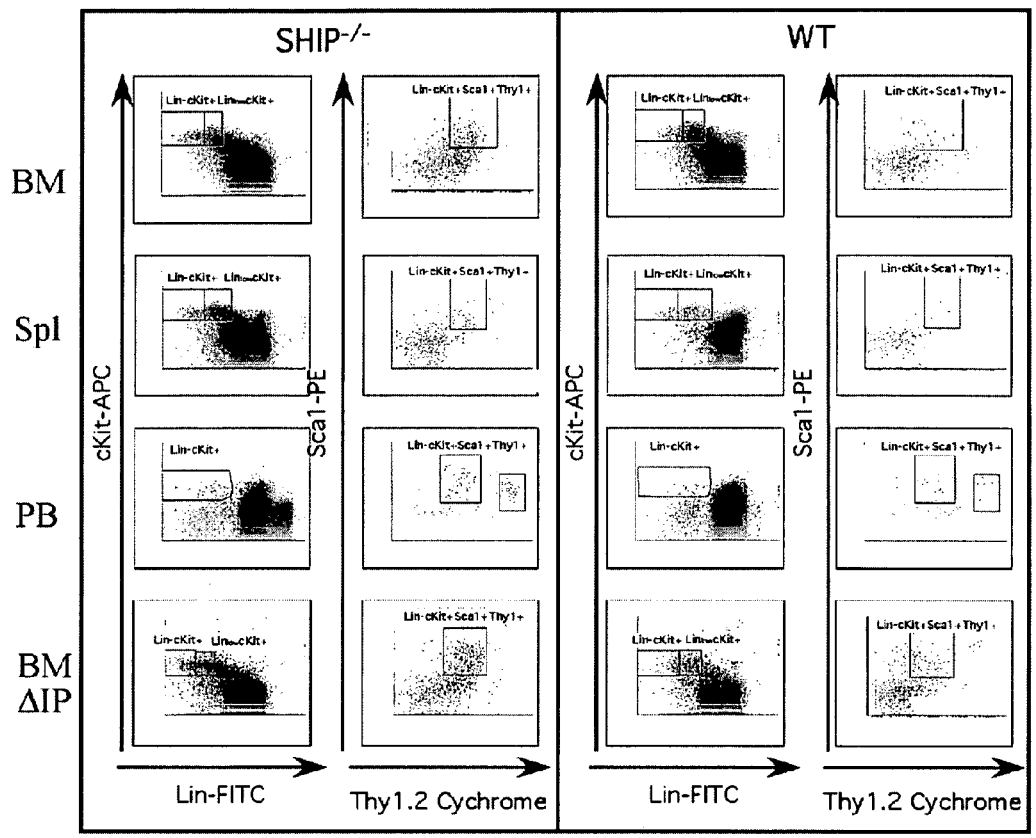
FIG. 5(A) shows results of analysis of bone marrow (BM), spleen, and peripheral blood (PB) from SHIP −/− H2B mice for the presence of hematopoietic stem cells (HSC;KTLS: Lin-cKit+Sca1+Thy1+) and early progenitor cells (Lin-cKit+) and late progenitor cells (LinlowcKit+) by flow cytometry analysis.
FIG. 5(B) shows results of analysis of marrow from SHIPDIP/DIP for HSC and progenitor cells as mentioned for BM H2B.
Figure 5C:
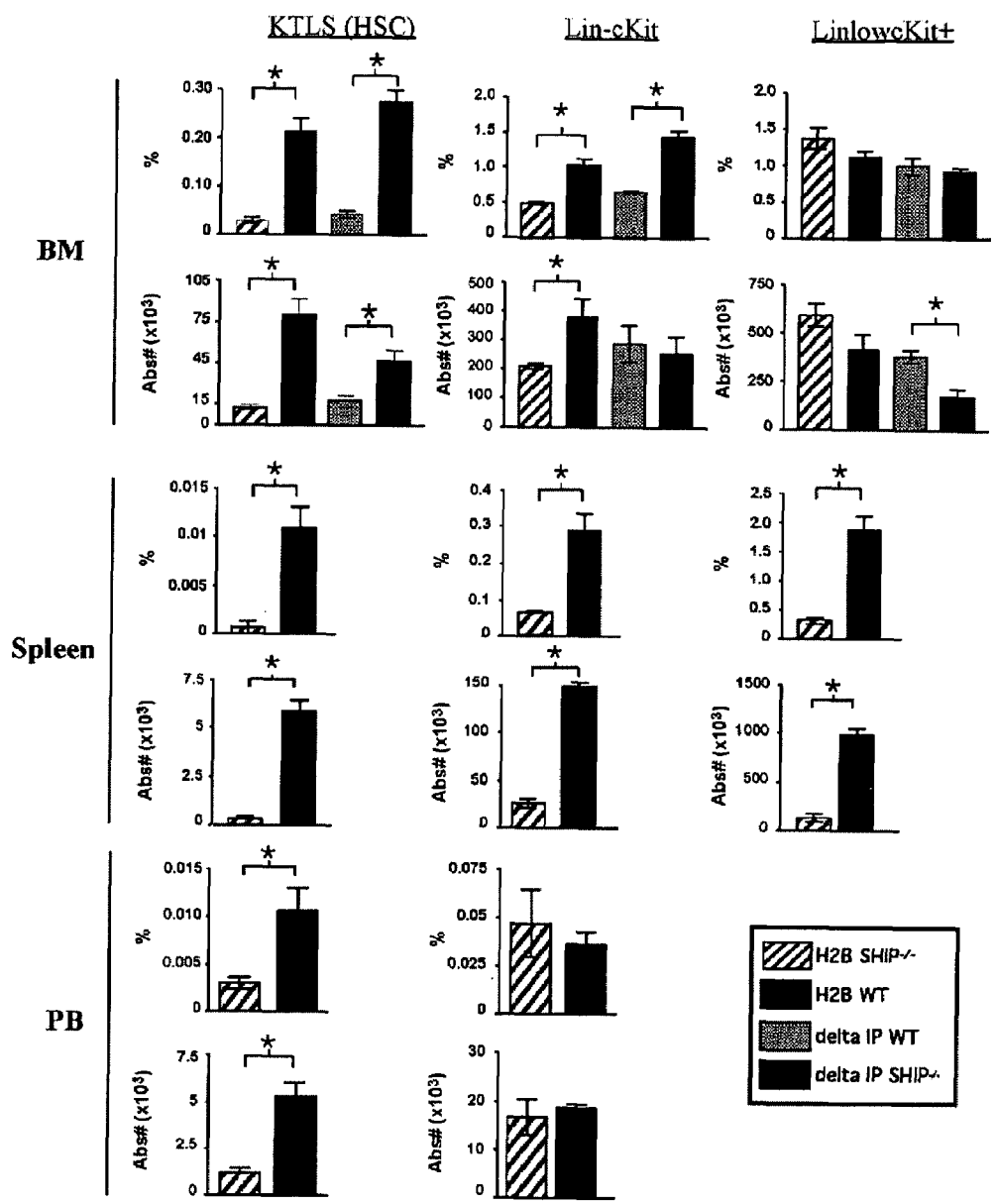
FIG. 5(C) shows results of statistical analysis showing the relative and absolute numbers of HSC and progenitor cells of different hematopoietic organs. The statistical analysis was performed using the unpaired Student T test. Results were considered significant (indicated by an *) when p values were under 0.005.
Figure 9:
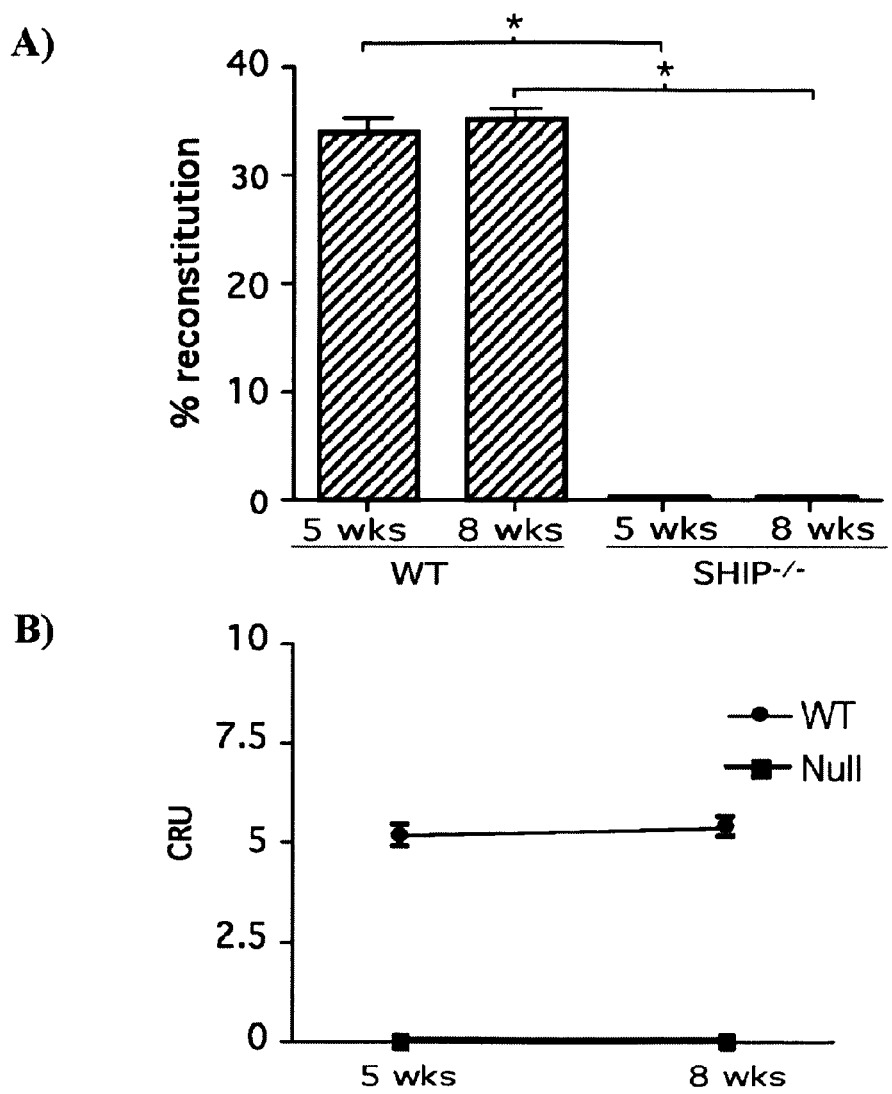
FIG. 9 shows the results of a competitive repopulation assay
Figure 10:
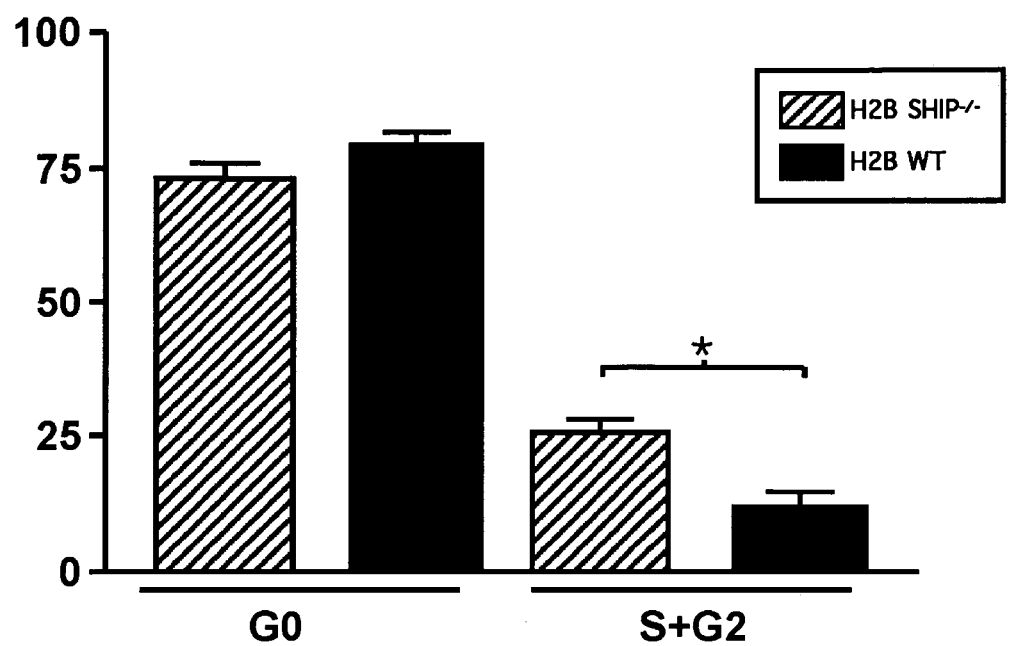
FIG. 10 is a cell cycle analysis on bone marrow from SHIP deficient and wild type mice.

FIGS. 2 and 10 show that the frequency of HSC that are actively cycling is increased and that HSC numbers are increased in the blood (FIG. 5). These findings show SHIP inhibition could be used to increase the number of cycling (i.e. actively-dividing) stem cells and thus their mobilization to the peripheral blood. The cycling of other stem cell types (mesenchymal, mammary, neural or organ-specific stem cells) may also be increased by SHIP-deficiency and thus non-hematopoietic stem cells may also be mobilized from their tissue of origin to the peripheral blood (thus, enabling non-invasive harvesting methods for non-hematopoietic stem cells by leukapheresis). Accordingly, temporary period of SHIP increases the cycling rate of endogenous stem cell populations and their mobilization to the blood for harvest. However, this period of SHIP inhibition should only be temporary (~1-2 weeks), as prolonged SHIP-deficiency (6-10 weeks) likely causes aging of endogenous stem cells as seen by the reduced ability of HSC in adult SHIP-deficient mice to repopulate the blood or tissue of interest (see FIGS. 8,9).

Alternatively, endogenous stem cells may not need to be harvested for subsequent return to the patient. The patient could be treated for a temporary period with SHIP inhibitors to increase the cycling of HSC to allow more rapid recovery of key blood cell populations (e.g. platelets, granulocytes, erythroid cells) after myeloablation. The same principle could also be applied to other stem cell populations in diseases where damage to tissues can be repaired by increasing the cycling and repopulation capacity of the stem cells for that tissue.

The ability of normal HSC to contribute to normal blood cell production is damaged by prolonged SHIP deficiency (9-12 weeks). This may occur by increasing the division rate of these cells and therefore prematurely "aging" these cells. Therefore, prolonged SHIP deficiency might also be used to burn out or "age" leukemic or tumor stem cell clones that must replenish cells of the leukemia or tumor. SHIP inhibitors might be combined with chemotherapeutic or other anti-cancer agents.

Treatment with SHIP inhibitors could also be used to age endogenous stem cell populations so that stem cell transplants (autologous or allogeneic) could compete more effectively for the tissues niches that support stem cell engraftment.

EXAMPLE 5

SHIP Deficiency Increases the Absolute Number of HSC In Vivo, Increases their Relative Proportion and Mobilizes HSC to the Peripheral Blood FIG. 5 (A) shows bone marrow (BM), spleen, and peripheral blood (PB) from SHIP−/− H2B mice were analyzed for the presence of hematopoietic stem cells (HSC; KTLS:Lin−cKit+Sca1+Thy1+) and early progenitor cells (Lin−cKit+) and late progenitor cells (LinlowcKit+) by flow cytometry analysis. B) Bone marrow from SHIPDIP/DIP was analyzed for HSC and progenitor cells as mentioned for BM H2B. C) Statistical analysis showing the relative and absolute numbers of HSC and progenitor cells different hematopoietic organs. The statistical analysis was performed using the unpaired Student T test. Results were considered significant (indicated by an *) when p values were under 0.05.

EXAMPLE 6

Method and Results of SHIP Ablation During Adulthood (In Vivo)

Figure 6:
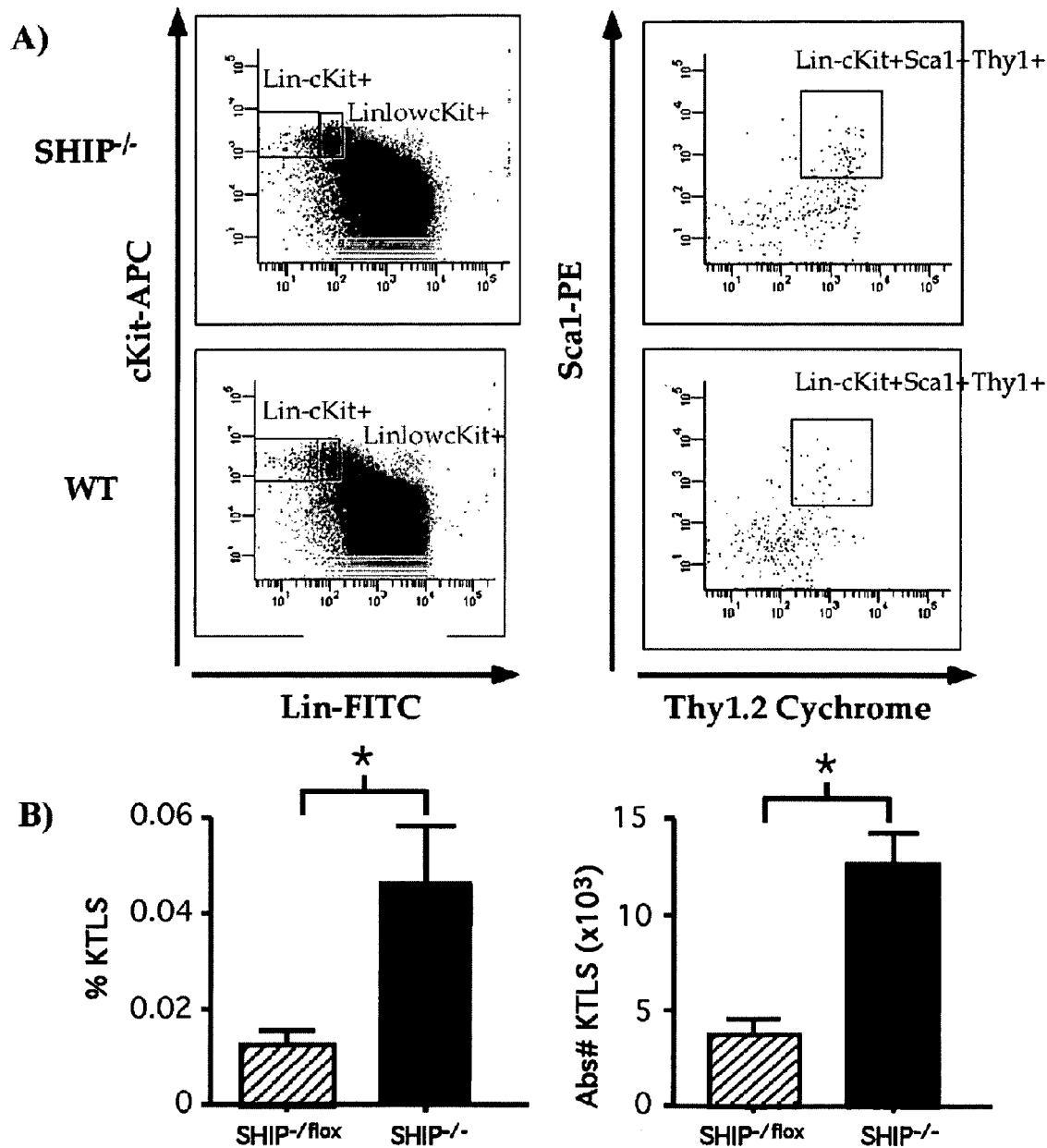
FIG. 6(A) shows flow cytometry analysis of SHIP deficient bone marrow. (B) Student T test results of the numbers of HSC.

In FIG. 6 HSC; KTLS (Lin−cKit+Sca1+Thy1+) cells are increased in mice in which SHIP was ablated during adulthood. (A) Bone marrow (BM) from Mx-CRE SHIP−/− and SHIP+/− mice were analyzed for the presence of hematopoietic stem cells (HSC; Lin−cKit+Sca1+Thy1+) by flow cytometry analysis. Mx-CRE SHIP−/− mice are created by injecting MxCRE SHIPFlox/− mice with polyIC, which induces the production of interferon. Interferon acts on the Mx promoter to cause the transcription of CRE. CRE will then cause recombination of the flox site, leading to SHIP deletion. This model allow use to study the effect of SHIP removal during adulthood. B) Statistical analysis showing the relative numbers of HSC from Mx-CRE SHIP−/− and SHIP−/flox.

The statistical analysis was performed using the unpaired Student t test in Prism 4. Results were considered significant when $p<0.005$. $*p<0.05$.

Figure 7A:
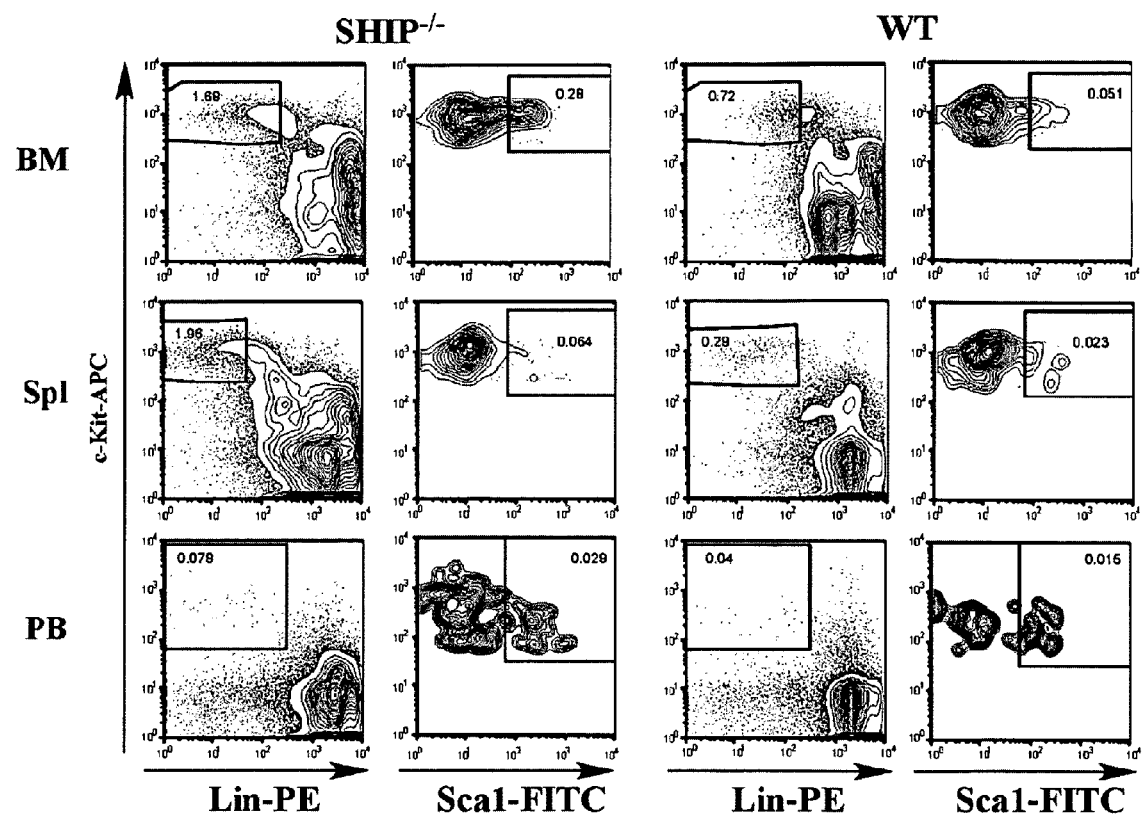
FIG. 7 represents results from statistical analysis of the numbers (relative/absolute) of HSC in varying hematopoietic organs.
Figure 7B:
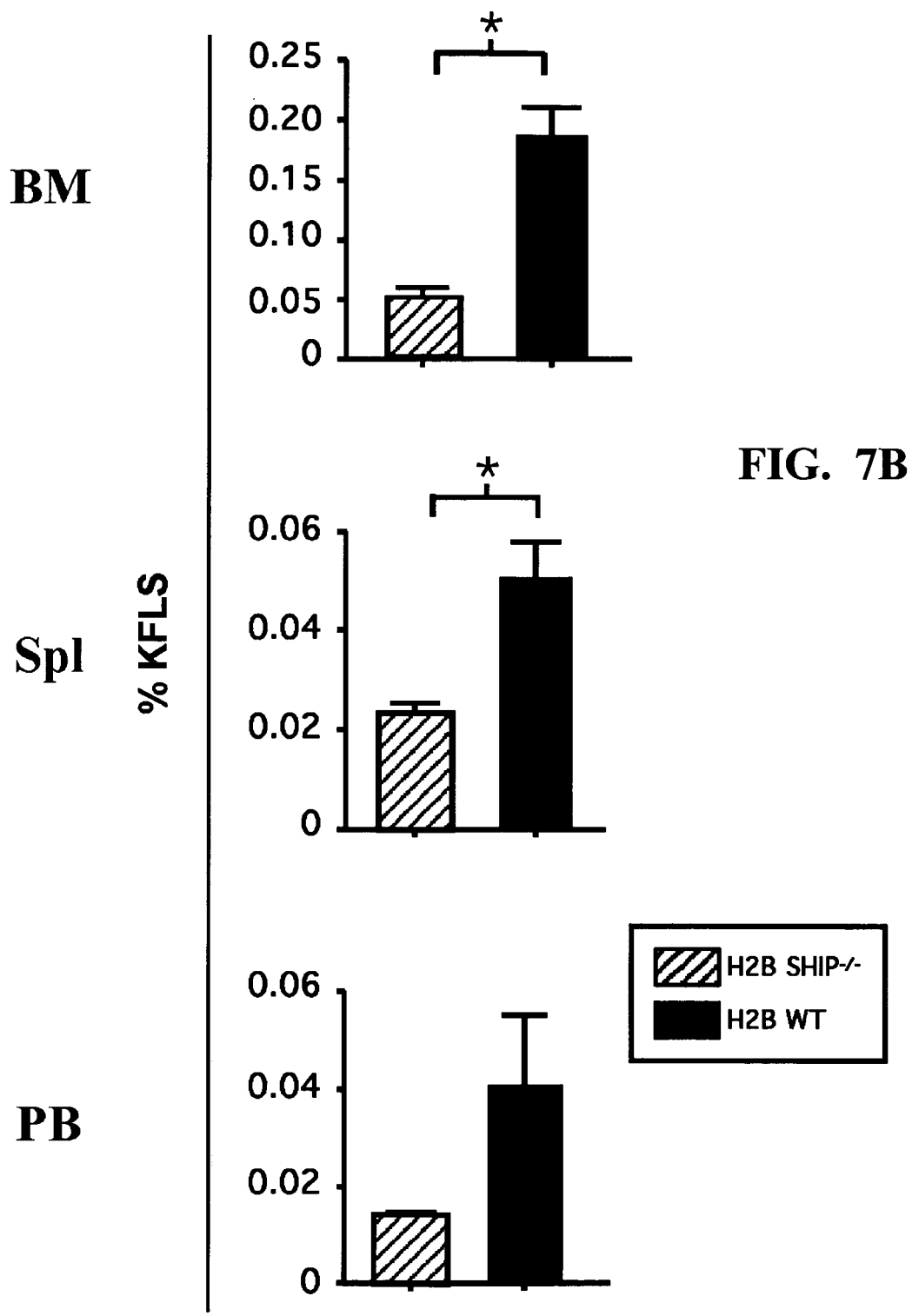
Figure 7C:
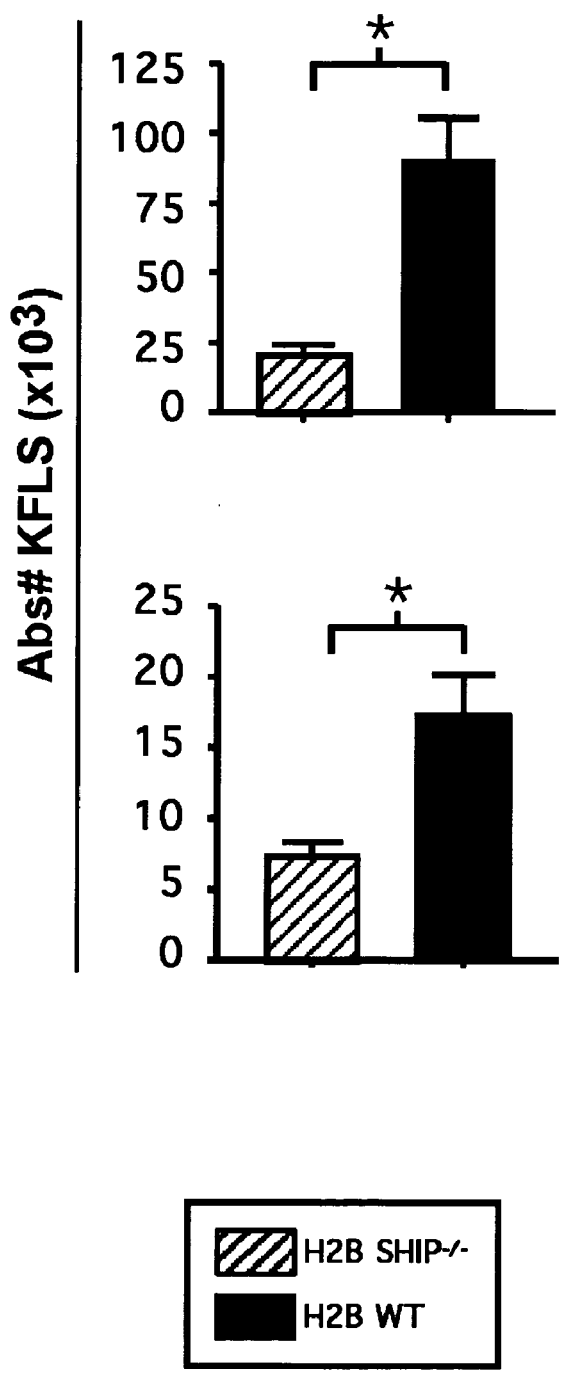

In FIG. 7 the same group that defined the KTLS phenotype, found another method to isolate immunophenotype to isolate HSC, which is Lin-Flk2−cKit+Sca1+(LFKS). LFKS cells are also increased in the SHIP−/− mice. (A) Bone marrow (BM), spleen, and peripheral blood (PB) from SHIP−/− H2B mice were analyzed for the presence of hematopoietic stem cells following a different immunophenotype (HSC; Lin−Flk2−cKit+Sca1+) by flow cytometry analysis, on FacsCalibur. B) Statistical analysis showing the relative numbers of HSC in the different hematopoietic organs. C) Statistical analysis showing the absolute numbers of HSC in the different hematopoietic organs. The statistical analysis was performed using the unpaired Student T test. Results were considered significant (indicated by an *) when p values were under 0.05.

Figure 8:
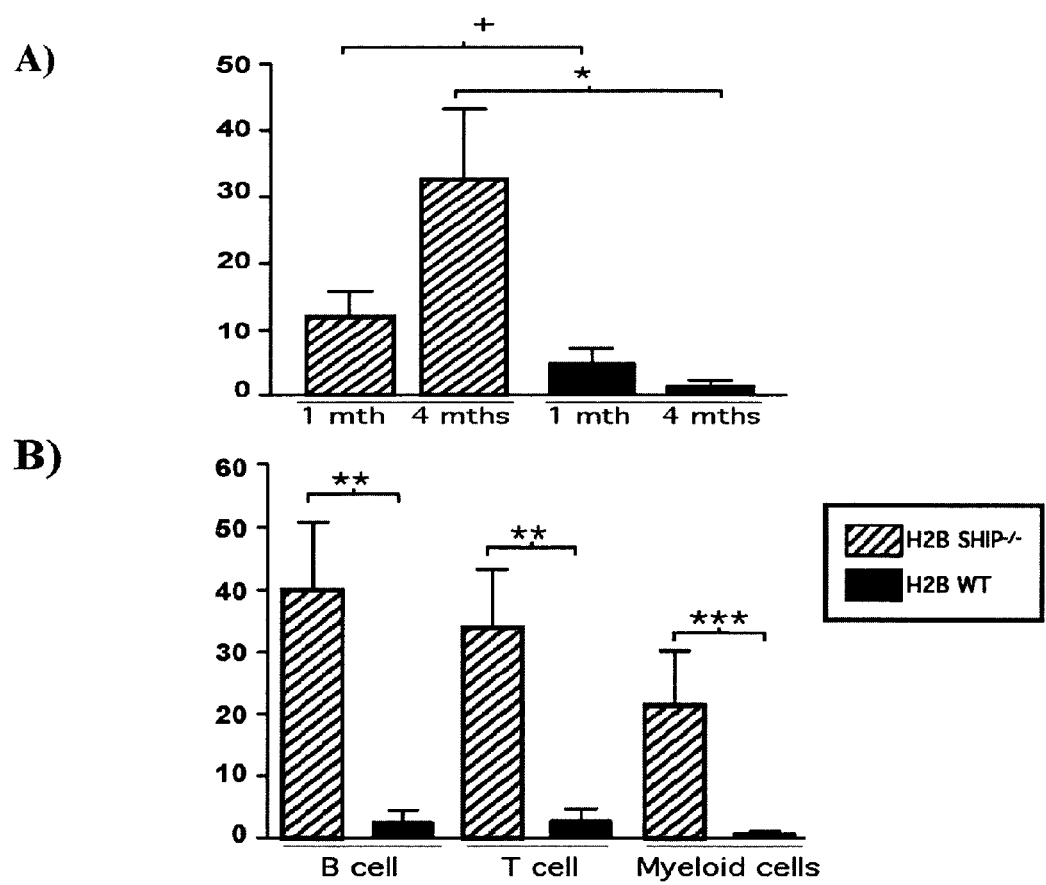
FIG. 8 shows the level of reconstitution after a direct competition assay.

FIG. 8 shows the level of reconstitution after direct competition assay. Direct competition assay was performed by sorting KTLS (Lin−cKit+Sca1+Thy1+) cells from SHIP−/−Ly5.2 mice and from WT Ly5.1 mice. 200 SHIP−/− Ly5.2 and 200 WT Ly5.1 KTLS were then injected into the same animal with 40 000 Sca1− supporting cells (Ly5.1/Ly5.2). The recipient mice were Ly5.1/Ly5.2, which allow us to identify which cells in the immune system comes from the recipient, WT donor or SHIP−/− donor. The recipient mice had undergone total body irradiation (dose: 600 rads and 2 hours later 400 rads) 2 hours before being transplanted with the test cells. After transplantation the mice were given antibiotic water to prevent opportunistic pathogen. At different time point after transplantation, the mice were tested for reconstitution of the hematopoietic compartment. A) Global reconstitution 4 weeks and 4 month after transplantation. The results show no significant difference 4 weeks after transplantation between the WT and the SHIP−/− HSC ability to reconstitute the hematopoietic system.

Four (4) months after transplantation, the proportion of hematopoietic cells derived from the WT KTLS is significantly higher than the one derived from SHIP−/− KTLS cells. B) shows the level of reconstitution, 4 months after transplantation, in 3 different hematopoietic lineage to show that the cells are pluripotent. Again the level of reconstitution from the WTKTLS is significantly higher than from SHIP−/− KTLS. This is the result of 11 mice done in two different experiments. Statistical significance was established using Prism 4 software, unpaired student t test. $+p>0.05$, $*p<0.01$, $p<0.005$, $*p<0.05$.

EXAMPLE 7

Long Term Competition Effects of SHIP Deficiency

FIG. 9 is a competitive repopulation assay showing that SHIP−/− bone marrow has less CRU than WT littermates BM. Mice transplanted: Ly5.1 C57Bl6 mice that were irradiated with one-single dose of 950 rads. The tested cells were Ly5.2 cells from either SHIP−/− mice or WT mice and the competing cells were Ly5.1.

(A) Level of reconstitution of the hematopoietic system by the tested donor BM. WT BM level of reconstitution is significantly higher than for SHIP−/− BM. Student t test $p<0.0001$. (B) Number of competitive repopulation unit (CRU) was established following a method developed by D. E. Harrison, where donor CRU=(10×% donor)/(100−% donor). 10 is the number of of CRU present in the competing BM (Ly5.1). WT BM has a significantly higher number of CRU compared to SHIP−/− mice. Unpaired t test $p=0.0005$.

FIG. 10 demonstrates that cell cycle analysis on BM from SHIP deficient and WT mice revealed that a greater proportion of SHIP−/− HSC in cell cycle. Bar graph representing the proportion of Lin−cKit+Sca1+cells that are G0 (resting) or in S/G2 phase (dividing). This graph includes results from experiment performed using SHIP−/− mice on a C57Bl6 background and SHIPDIP/DIP on a 129SvJ background with respective WT counterparts.

EXAMPLE 8

Effects of SHIP Deficiency in Non-HSC

Figure 11:
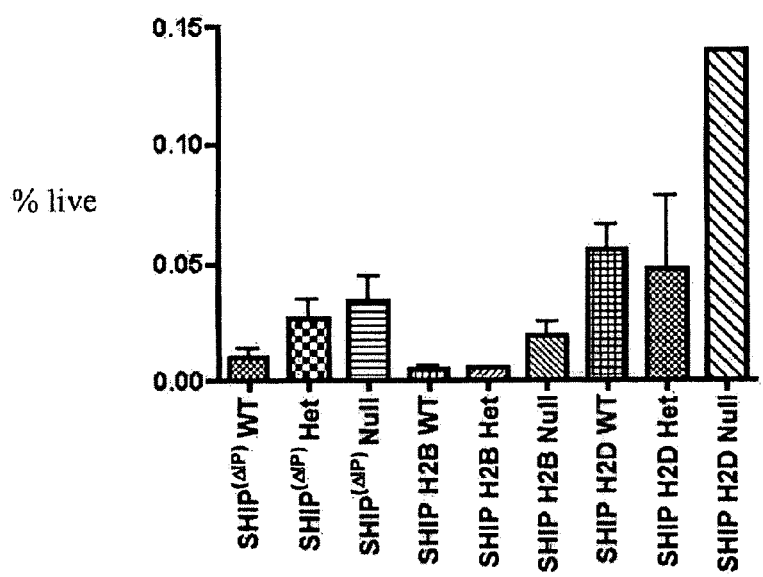
FIG. 11 shows that SHIP deficiency alters the size of the mammary stem cell compartment.

FIG. 11 shows that mammary stem cells were analyzed from both H2B and H2D SHIP mice and from ÆIP (Rock) mice. Cells were isolated from the third and fourth mammary glands of 6-8 week old female mice. The glands were made into a single cell suspension through physical processing and enzymatic digestion. The mammary gland single cell suspension was examined for MaSC using the lineage negative gate of CD45−, and two positive gates SP+ and Sca+.

Figure 12:
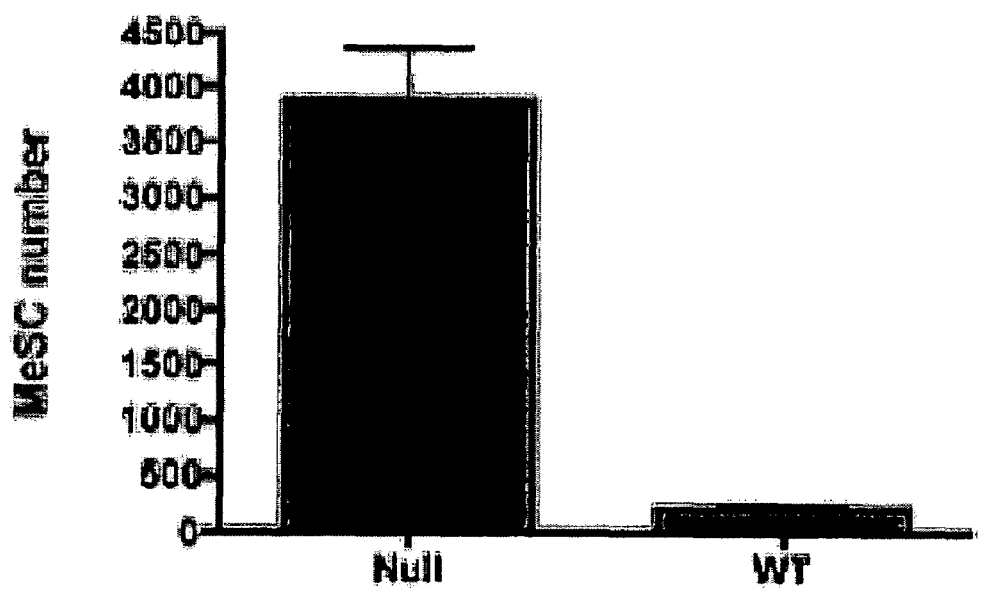
FIG. 12 shows that SHIP deficiency leads to an increase in mesnechymal stem cell numbers.

FIG. 12 MeSC were analyzed from SHIP+/+ and SHIP−/− mice on a C57Bl6/J background. Femurs and tibiae were collected from three sets of mice. The muscle, cartilage, and marrow were removed. The bone was crushed with a mortar and pestle and the fragments were digested with collagenase. Cells were plated with MeSC isolation media in triplicate at equal density. They were allowed to attach for 24 hours at the conclusion of which the non-adherent cells were washed away and the adherent cells were counted. A students t-test was performed and the P-value <0.0001.

Figure 13:
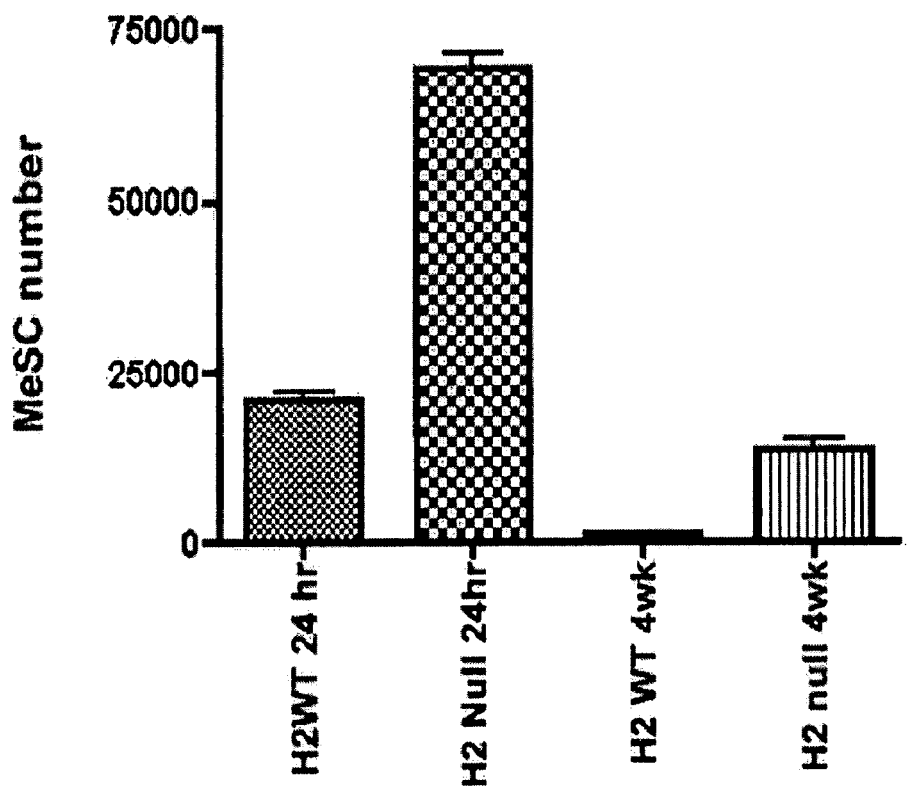
FIG. 13 is an analysis of SHIP+/= and SHIP−/− Mesenchymal stem cells.

FIG. 13 represents the analysis of SHIP+/= and SHIP−/− MeSC. Bar graphs represent the number of MeSC per 1 million input whole bone marrow cells plated at time zero. Cells were counted, after lifting with trypsin, at 24 hours and 4 weeks post time zero using a hematocytometer. Total cell numbers decreased at 4 weeks as the cultures became a more homogenous population, though the difference that exists between the SHIP+/+ and SHIP−/− cell counts at each time point increased from a factor of 3.2 for the WT to 11.7 for the null which has a p value of p<0.003 indicating that this increase is significant. *p<0.0001**p<0.01 by a two-tailed students t-test.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be the to fall therebetween. Now that the invention has been described.

The invention claimed is:

1. A method of increasing the number of hematopoietic stem cells in peripheral blood of a patient, comprising administering an effective amount of an RNA interference molecule targeting SH2-domain containing inositol 5-phosphatase (SHIP) to the patient, wherein the number of hematopoietic stem cells in the peripheral blood of the patient is thereby increased.

2. The method of claim 1, further comprising harvesting the hematopoietic stem cells from the patient after said administering.

3. The method of claim 2, wherein said harvesting comprises leukopheresis.

4. The method of claim 2, further comprising administering the harvested hematopoietic stem cells to the patient.

5. The method of claim 1, wherein the RNA interference molecule is administered intravenously.

6. The method of claim 1, wherein said administering mobilizes the hematopoietic stem cells to the peripheral blood.

7. The method of claim 1, wherein the patient has undergone myeloablation prior to said administering.

8. The method of claim 1, wherein the RNA interference molecule is administered to the patient for 1 week or 2 weeks.

9. The method of claim 1, wherein the subject has cancer or an autoimmune deficiency.

10. The method of claim 4, wherein the subject has cancer or an autoimmune deficiency.

* * * * *

UNITED STATES PATENT AND TRADEMARK OFFICE
CERTIFICATE OF CORRECTION

PATENT NO. : 7,691,821 B2 Page 1 of 1
APPLICATION NO. : 10/709801
DATED : April 6, 2010
INVENTOR(S) : Caroline Desponts et al.

It is certified that error appears in the above-identified patent and that said Letters Patent is hereby corrected as shown below:

Column 12,
    Line 8, "Now that the invention has been described." should read
        --Now that the invention has been described,--.

Signed and Sealed this

Twenty-second Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,691,821 B2  
APPLICATION NO. : 10/709801  
DATED : April 6, 2010  
INVENTOR(S) : Caroline Desponts et al.

Page 1 of 1

It is certified that error appears in the above-identified patent and that said Letters Patent is hereby corrected as shown below:

Column 1,  
Lines 20-27,  "STATEMENT OF GOVERNMENT INTEREST

The invention described herein may be manufactured and used by the Government of the United States of America for governmental purposes without payment of any royalties thereon.

BACKGROUND ART"

should read

--STATEMENT OF GOVERNMENT INTEREST

This invention was made with government support under R01 DK054767 and R01 HL072523 awarded by the National Institutes of Health. The government has certain rights in the invention.

BACKGROUND ART--.

Signed and Sealed this  
Twentieth Day of December, 2011

David J. Kappos  
*Director of the United States Patent and Trademark Office*

```
                              SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: SHIP1 siRNA target sequences.  Predicted to
      have good specificity and good knockdown against the human SHIP1
      cDNA sequence.

<400> SEQUENCE: 1
gcctgttgtc atccattga                                                  19

<210> SEQ ID NO 2
<211> LENGTH: 19
<212> TYPE: DNA
<213> ORGANISM: Artificial Sequence
<220> FEATURE:
<223> OTHER INFORMATION: SHIP1 siRNA target sequences.  Predicted to
      have good specificity and good knockdown against the human SHIP1
      cDNA sequence.

<400> SEQUENCE: 2
ataagttggt gatcttggt                                                  19

<210> SEQ ID NO 3
<211> LENGTH: 19
<212> TYPE: DNA
<213> ORGANISM: Artificial Sequence
<220> FEATURE:
<223> OTHER INFORMATION: SHIP1 siRNA target sequences.  Predicted to
      have good specificity and good knockdown against the human SHIP1
      cDNA sequence.

<400> SEQUENCE: 3
gccacatctg tactgacaa                                                  19

<210> SEQ ID NO 4
<211> LENGTH: 19
<212> TYPE: DNA
<213> ORGANISM: Artificial Sequence
<220> FEATURE:
<223> OTHER INFORMATION: SHIP1 siRNA target sequences.  Predicted to
      have good specificity and good knockdown against the human SHIP1
      cDNA sequence.

<400> SEQUENCE: 4
agacaggcat tgcaaacac                                                  19

<210> SEQ ID NO 5
<211> LENGTH: 19
<212> TYPE: DNA
<213> ORGANISM: Artificial Sequence
<220> FEATURE:
<223> OTHER INFORMATION: SHIP1 siRNA target sequences.  Predicted to
      have good specificity and good knockdown against the human SHIP1
```

-continued cDNA sequence.

<400> SEQUENCE: 5
acatcactca ccgcttcac                                                    19

<210> SEQ ID NO 6
<211> LENGTH: 19
<212> TYPE: DNA
<213> ORGANISM: Artificial Sequence
<220> FEATURE:
<223> OTHER INFORMATION: SHIP1 siRNA target sequences. Predicted to
      have good specificity and good knockdown against the human SHIP1
      cDNA sequence.

<400> SEQUENCE: 6
tcttaactac cgtgtggat                                                    19

<210> SEQ ID NO 7
<211> LENGTH: 19
<212> TYPE: DNA
<213> ORGANISM: Artificial Sequence
<220> FEATURE:
<223> OTHER INFORMATION: SHIP1 siRNA target sequences. Predicted to
      have good specificity and good knockdown against the human SHIP1
      cDNA sequence.

<400> SEQUENCE: 7
aatacgccta caccaagca                                                    19

<210> SEQ ID NO 8
<211> LENGTH: 19
<212> TYPE: DNA
<213> ORGANISM: Artificial Sequence
<220> FEATURE:
<223> OTHER INFORMATION: SHIP1 siRNA target sequences. Predicted to
      have good specificity and good knockdown against the human SHIP1
      cDNA sequence.

<400> SEQUENCE: 8
gtaccagcga catcatgac                                                    19

<210> SEQ ID NO 9
<211> LENGTH: 19
<212> TYPE: DNA
<213> ORGANISM: Artificial Sequence
<220> FEATURE:
<223> OTHER INFORMATION: SHIP1 siRNA target sequences. Predicted to
      have good specificity and good knockdown against the human SHIP1
      cDNA sequence.

<400> SEQUENCE: 9
gcgacatcat gacgagtga                                                    19

<210> SEQ ID NO 10
<211> LENGTH: 19
<212> TYPE: DNA
<213> ORGANISM: Artificial Sequence
<220> FEATURE:
<223> OTHER INFORMATION: SHIP1 siRNA target sequences. Predicted to
      have good specificity and good knockdown against the human SHIP1
      cDNA sequence.

<400> SEQUENCE: 10
aggacagatt gagtttctc                                                    19

<210> SEQ ID NO 11
<211> LENGTH: 19

```
<212> TYPE: DNA
<213> ORGANISM: Artificial Sequence
<220> FEATURE:
<223> OTHER INFORMATION: SHIP1 siRNA target sequences. Predicted to
      have good specificity and good knockdown against the human SHIP1
      cDNA sequence.

<400> SEQUENCE: 11
ggtgctatgc cacattgaa                                                 19

<210> SEQ ID NO 12
<211> LENGTH: 19
<212> TYPE: DNA
<213> ORGANISM: Artificial Sequence
<220> FEATURE:
<223> OTHER INFORMATION: SHIP1 siRNA target sequences. Predicted to
      have good specificity and good knockdown against the human SHIP1
      cDNA sequence.

<400> SEQUENCE: 12
gtttggtgag actcttcca                                                 19

<210> SEQ ID NO 13
<211> LENGTH: 19
<212> TYPE: DNA
<213> ORGANISM: Artificial Sequence
<220> FEATURE:
<223> OTHER INFORMATION: SHIP1 siRNA target sequences. Predicted to
      have good specificity and good knockdown against the human SHIP1
      cDNA sequence.

<400> SEQUENCE: 13
agacggagcg tgatgaatc                                                 19

<210> SEQ ID NO 14
<211> LENGTH: 4870
<212> TYPE: DNA
<213> ORGANISM: Homo sapiens

<400> SEQUENCE: 14
gtggaggggc ctccgctccc ctcggtggtg tgtgggtcct gggggtgcct gccggcccag    60
ccgaggaggc ccacgcccac catggtcccc tgctggaacc atggcaacat cacccgctcc   120
aaggcggagg agctgctttc caggacaggc aagggcacga gcttcctcgt gcgtgccagc   180
gagtccatct cccgggcata cgcgctctgc gtgctgtatc ggaattgcgt ttacacttac   240
agaattctgc caatgaagat gataaattc actgttcagg catccgaagg cgtctccatg   300
aggttcttca ccaagctgga ccagctcatc gagttttaca agaaggaaaa catggggctg   360
gtgacccatc tgcaataccc tgtgccgctg gaggaagagg acacaggcga cgaccctgag   420
gaggacacag tagaaagtgt cgtgtctcca cccgagctgc ccccaagaaa catcccgctg   480
actgccagct cctgtgaggc caaggaggtt cctttttcaa cgagaatcc ccgagcgacc   540 gagaccagcc ggccgagcct ctccgagaca ttgttccagc gactgcaaag catggacacc   600
agtgggcttc cagaagagca tcttaaggcc atccaagatt atttaagcac tcagctcgcc   660
caggactctg aatttgtgaa gacagggtcc agcagtcttc ctcacctgaa gaaactgacc   720
acactgctct gcaaggagct ctatggagaa gtcatccgga ccctcccatc cctggagtct   780
ctgcagaggt tatttgacca gcagctctcc ccgggcctcc gtccacgtcc tcaggttcct   840
ggtgaggcca atccccatca catggtgtcc aagctcagcc aactgacaag cctgttgtca   900
tccattgaag acaaggtcaa ggccttgctg cacgagggtc ctgagtctcc gcaccggccc   960
```

-continued

```
tcccttatcc ctccagtcac ctttgaggtg aaggcagagt ctctggggat tcctcagaaa    1020
atgcagctca aagtcgacgt tgagtctggg aaactgatca ttaagaagtc caaggatggt    1080
tctgaggaca agttctacag ccacaagaaa atcctgcagc tcattaagtc acagaaattt    1140
ctgaataagt tggtgatctt ggtggaaaca gagaaggaga agatcctgcg gaaggaatat    1200 gttttttgctg actccaaaaa gagagaaggc ttctgccagc tcctgcagca gatgaagaac    1260
aagcactcag agcagccgga gcccgacatg atcaccatct tcatcggcac ctggaacatg    1320
ggtaacgccc cccctcccaa gaagatcacg tcctggtttc tctccaaggg gcagggaaag    1380
acgcgggacc actctgcgga ctacatcccc catgacattt acgtgatcgg cacccaagag    1440
gaccccctga gtgagaagga gtggctggag atcctcaaac actccctgca agaaatcacc    1500
agtgtgactt ttaaaacagt cgccatccac acgctctgga acatccgcat cgtggtgctg    1560
gccaagcctg agcacgagaa ccggatcagc cacatctgta ctgacaacgt gaagacaggc    1620
attgcaaaca cactggggaa caaggggagcc gtggggtgt cgttcatgtt caatggaacc    1680
tccttagggt tcgtcaacag ccacttgact tcaggaagtg aaaagaaact caggcgaaac    1740
caaaactata tgaacattct ccggttcctg gccctgggcg acaagaagct gagtcccttt    1800
aacatcactc accgcttcac gcacctcttc tggtttgggg atcttaacta ccgtgtggat    1860
ctgcctacct gggaggcaga aaccatcatc cagaaaatca gcagcagca gtacgcagac    1920 ctcctgtccc acgaccagct gctcacagag aggagggagc agaaggtctt cctacacttc    1980
gaggaggaag aaatcacgtt tgccccaacc taccgttttg agagactgac tcgggacaaa    2040
tacgcctaca ccaagcagaa agcgacaggg atgaagtaca acttgccttc ctggtgtgac    2100
cgagtcctct ggaagtctta tccctggtg cacgtggtgt gtcagtctta tggcagtacc    2160
agcgacatca tgacgagtga ccacagccct gtctttgcca catttgaggc aggagtcact    2220
tcccagtttg tctccaagaa cggtcccggg actgttgaca gccaaggaca gattgagttt    2280
ctcaggtgct atgccacatt gaagaccaag tcccagacca aattctacct ggagttccac    2340
tcgagctgct tggagagttt tgtcaagagt caggaaggag aaaatgaaga aggaagtgag    2400
ggggagctgg tggtgaagtt tggtgagact cttccaaagc tgaagcccat tatctctgac    2460
cctgagtacc tgctagacca gcacatcctc atcagcatca gtcctctga cagcgacgaa    2520 tcctatggcg agggctgcat tgcccttcgg ttagaggcca cagaaacgca gctgcccatc    2580
tacacgcctc tcacccacca tgggagttg acaggccact tccaggggga gatcaagctg    2640
cagacctctc agggcaagac gagggagaag ctctatgact ttgtgaagac ggagcgtgat    2700
gaatccagtg ggccaaagac cctgaagagc ctcaccagcc acgacccat gaagcagtgg    2760 gaagtcacta gcagggcccc tccgtgcagt ggctccagca tcactgaaat catcaacccc    2820
aactacatgg gagtggggcc ctttgggcca ccaatgcccc tgcacgtgaa gcagaccttg    2880 tccccctgacc agcagcccac agcctggagc tacgaccagc cgcccaagga ctccccgctg    2940
gggccctgca ggggagaaag tcctccgaca cctcccggcc agccgcccat atcacccaag    3000
aagtttttac cctcaacagc aaaccggggt ctccctccca ggacacagga gtcaaggccc    3060
agtgacctgg ggaagaacgc aggggacacg ctgcctcagg aggacctgcc gctgacgaag    3120
cccgagatgt ttgagaaccc cctgtatggg tccctgagtt ccttccataa gcctgctccc    3180
aggaaggacc aggaatcccc caaaatgccg cggaaggaac cccgccctg cccggaaccc    3240 ggcatcttgt cgcccagcat cgtgctcacc aaagcccagg aggctgatcg cggcgagggg    3300
cccggcaagc aggtgcccgc gccccggctg cgctccttca cgtgctcatc ctctgccgag    3360
```

```
ggcagggcgg ccggcgggga caagagccaa gggaagccca agaccccggt cagctcccag    3420
gccccggtgc cggccaagag gcccatcaag ccttccagat cggaaatcaa ccagcagacc    3480
ccgcccaccc cgacgccgcg gccgccgctg ccagtcaaga gcccggcggt gctgcacctc    3540
cagcactcca agggccgcga ctaccgcgac aacaccgagc tcccgcatca cggcaagcac    3600
cggccggagg aggggccacc agggcctcta ggcaggactg ccatgcagtg aagccctcag    3660
tgagctgcca ctgagtcggg agcccagagg aacggcgtga agccactgga ccctctcccg    3720
ggacctcctg ctggctcctc ctgcccagct tcctatgcaa ggctttgtgt tttcaggaaa    3780
gggcctagct tctgtgtggc ccacagagtt cactgcctgt gagacttagc accaagtgct    3840
gaggctggaa gaaaacgca caccagacgg gcaacaaaca gtctgggtcc ccagctcgct    3900
cttggtactt gggacccag tgcctcgttg agggcgccat tctgaagaaa ggaactgcag    3960
cgccgatttg agggtggaga tatagataat aataatatta ataataataa tggccacatg    4020
gatcgaacac tcatgatgtg ccaagtgctg tgctaagtgc tttacgaaca ttcgtcatat    4080
caggatgacc tcgagagctg aggctctagc cacctaaaac cacgtgccca aacccaccag    4140
tttaaaacgg tgtgtgttcg gaggggtgaa agcattaaga agcccagtgc cctcctggag    4200
tgagacaagg gctcggcctt aaggagctga agagtctggg tagcttgttt agggtacaag    4260
aagcctgttc tgtccagctt cagtgacaca agctgcttta gctaaagtcc cgcgggttcc    4320
ggcatggcta ggctgagagc agggatctac ctggcttctc agttctttgg ttggaaggag    4380
caggaaatca gctcctattc tccagtggag agatctggcc tcagcttggg ctagagatgc    4440
caaggcctgt gccaggttcc ctgtgccctc ctcgaggtgg gcagccatca ccagccacag    4500
ttaagccaag ccccccaaca tgtattccat cgtgctggta gaagagtctt tgctgttgct    4560
cccgaaagcc gtgctctcca tcctggctgc cagggagggt gggcctcttg gttccaggct    4620
cttgaaatag tgcagccttt tcttcctatc tctgtggctt tcaactctgc ttccttggtt    4680
attaagagaa tagatgggtg atgtctttcc ttatgttgct ttttcaacat agcagaatta    4740
atgttgggag ctaaatccac tggtgtgtgt gaatgcagaa gggaatgcac cccaccttcc    4800
catgaatgaa gtctgcgtac caataaattg tgccttctcc tccaaaaaaa aaaaaaaaaa    4860
ataaaaaaaa                                                            4870
```